(12) United States Patent
Hashimoto et al.

(10) Patent No.: US 12,310,689 B2
(45) Date of Patent: May 27, 2025

(54) DIAGNOSIS/TREATMENT SUPPORT ROBOT, DIAGNOSIS/TREATMENT SUPPORT ROBOT SYSTEM, AND DIAGNOSIS/TREATMENT SUPPORT METHOD

(71) Applicant: KAWASAKI JUKOGYO KABUSHIKI KAISHA, Kobe (JP)

(72) Inventors: Yasuhiko Hashimoto, Kobe (JP); Atsushi Kameyama, Kobe (JP); Masayuki Kamon, Kobe (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 374 days.

(21) Appl. No.: 17/995,739

(22) PCT Filed: Apr. 9, 2021

(86) PCT No.: PCT/JP2021/015000
§ 371 (c)(1),
(2) Date: Oct. 7, 2022

(87) PCT Pub. No.: WO2021/206161
PCT Pub. Date: Oct. 14, 2021

(65) Prior Publication Data
US 2023/0165650 A1 Jun. 1, 2023

(30) Foreign Application Priority Data
Apr. 10, 2020 (JP) .................................. 2020-071351
May 29, 2020 (JP) .................................. 2020-094574

(51) Int. Cl.
*A61B 34/00* (2016.01)
*A61B 5/15* (2006.01)
(Continued)

(52) U.S. Cl.
CPC ........ *A61B 34/37* (2016.02); *A61B 5/150007* (2013.01); *A61B 90/37* (2016.02); *A61B 90/50* (2016.02); *A61B 2034/306* (2016.02)

(58) Field of Classification Search
CPC ......... A61B 34/37; A61B 90/37; A61B 90/50; A61B 5/150007; A61B 2034/306
See application file for complete search history.

(56) References Cited

U.S. PATENT DOCUMENTS 6,617,146 B1 * 9/2003 Naccarato .............. C12M 41/48
435/243
2012/0179187 A1 * 7/2012 Loushin ............. A61B 10/0045
606/185
(Continued)

FOREIGN PATENT DOCUMENTS

CN 108289716 A 7/2018
CN 209826974 U 12/2019
(Continued)

*Primary Examiner* — Truc M Do
(74) *Attorney, Agent, or Firm* — METROLEX IP LAW GROUP, PLLC; Robert L. Scott, Esq.

(57) ABSTRACT

A diagnosis/treatment support robot includes a surgical manipulator that is remotely manipulated by an operator. The surgical manipulator includes a robotic arm. The robotic arm includes an instrument mount at a tip thereof. A surgical instrument for surgery of a patient is attached to the instrument mount. An auxiliary instrument is attachable to the instrument mount. The auxiliary instrument is an instrument other than the surgical instrument. The auxiliary instrument is an instrument for at least either one of an auxiliary practice of a diagnosis of an infectious disease or an auxiliary practice of a treatment of the infectious disease for a target person.

14 Claims, 15 Drawing Sheets

(51) Int. Cl.
*A61B 34/37* (2016.01)
*A61B 90/00* (2016.01)
*A61B 90/50* (2016.01)
*A61B 34/30* (2016.01)

(56) References Cited

U.S. PATENT DOCUMENTS

| | | | |
|---|---|---|---|
| 2014/0005687 A1* | 1/2014 | Prisco | A61B 90/92 |
| | | | 901/41 |
| 2018/0177558 A1 | 6/2018 | McKinley et al. | |
| 2018/0193101 A1 | 7/2018 | Hashimoto | |
| 2018/0250086 A1* | 9/2018 | Grubbs | A61B 34/35 |
| 2018/0360550 A1 | 12/2018 | Nakanishi | |
| 2018/0360553 A1 | 12/2018 | Nakanishi | |
| 2020/0281667 A1 | 9/2020 | Blondel et al. | |

FOREIGN PATENT DOCUMENTS

| | | |
|---|---|---|
| JP | 2002-085353 A | 3/2002 |
| JP | 2005-261734 A | 9/2005 |
| JP | 2007-130282 A | 5/2007 |
| JP | 2017-104453 A | 6/2017 |
| WO | 2010/006211 A1 | 1/2010 |
| WO | 2017/002143 A1 | 1/2017 |
| WO | 2019/005921 A1 | 1/2019 |
| WO | 2019/092372 A1 | 5/2019 |
| WO | 2019/213023 A1 | 11/2019 |

* cited by examiner

NORMAL AREA

DIAGNOSIS/TREATMENT SUPPORT ROBOT, DIAGNOSIS/TREATMENT SUPPORT ROBOT SYSTEM, AND DIAGNOSIS/TREATMENT SUPPORT METHOD

CROSS-REFERENCE TO RELATED APPLICATIONS

This application claims priority to and the benefit of Japanese Patent Application No. 2020-071351 filed on Apr. 10, 2020 and Japanese Patent Application No. 2020-094574 filed on May 29, 2020, the entire disclosures of which are incorporated herein by reference.

TECHNICAL FIELD

The present disclosure relates to a diagnosis/treatment support robot, a diagnosis/treatment support robot system, and a diagnosis/treatment support method.

BACKGROUND ART

Robots that support auxiliary medical practices which are medical practices other than surgery are known. For example, PTL 1 discloses a blood collecting system in which a robot travels to supply to a blood collection base a blood collecting vessel storage tray which is for a patient in a room and is prepared by a blood collecting vessel preparation device.

CITATION LIST

Patent Literature

PTL 1: Japanese Laid-Open Patent Application Publication No. 2007-130282

SUMMARY OF INVENTION

Currently (April, 2020), an infectious disease caused by novel coronavirus (COVID-19) is spreading, and a large number of medical workers (doctors, nurses, etc.) are necessary for auxiliary practices of the diagnosis of the infectious disease and auxiliary practices of the treatment of the infectious disease. Moreover, in the case of the infectious diseases, the infection of the medical workers needs to be prevented. However, the above conventional robot cannot collect blood.

The present disclosure was made to solve the above problems, and an object of the present disclosure is to provide a diagnosis/treatment support robot, a diagnosis/treatment support robot system, and a diagnosis/treatment support method, each of which performs at least either one of an auxiliary practice of a diagnosis or an auxiliary practice of a treatment in place of a medical worker, and with this, prevents the medical worker from being infected with an infectious disease.

To achieve the above object, a diagnosis/treatment support robot according to one aspect of the present disclosure includes a surgical manipulator that is remotely manipulated by an operator. The surgical manipulator includes a robotic arm. The robotic arm includes an instrument mount at a tip thereof. A surgical instrument for surgery of a patient is attached to the instrument mount. An auxiliary instrument is attachable to the instrument mount. The auxiliary instrument is an instrument other than the surgical instrument. The auxiliary instrument is an instrument for at least either one of an auxiliary practice of a diagnosis of an infectious disease for a target person or an auxiliary practice of a treatment of the infectious disease for the target person.

According to this configuration, the auxiliary instrument can be attached to the instrument mount, and the operator can manipulate the surgical manipulator. With this, at least either one of the diagnosis of the infectious disease or the treatment of the infectious disease can be performed for the target person. As a result, the diagnosis/treatment support robot can perform at least either one of the diagnosis or the treatment in place of a medical worker. In addition, generally, the surgical manipulator can perform surgery of a patient by precise operation. Therefore, the auxiliary practice of the diagnosis or the auxiliary practice of the treatment can be appropriately performed even when it is slightly complex. The surgical manipulator may be located in an isolation area that isolates a person who is suspected to be infected (hereinafter referred to as a "suspected infected person") or an infected person (hereinafter such the isolation area may be simply referred to as the "isolation area"), and the operator may be located in a normal area that is not isolated and remotely manipulates the surgical manipulator. With this, the operator can be prevented from being infected with the infectious disease. As a result, the medical worker can be prevented from being infected with the infectious disease.

Moreover, the prevalence of the infectious disease is intermittent. Therefore, when the infectious disease is not prevalent, the surgical instrument is attached to the robotic arm, and the diagnosis/treatment support robot is used as a surgical robot as it should be used. Thus, the diagnosis/treatment support robot can be effectively used.

A diagnosis/treatment support robot system according to another aspect of the present disclosure includes: the above diagnosis/treatment support robot; and the auxiliary instrument.

According to this configuration, a diagnosis/treatment instrument can be attached to the surgical manipulator of the diagnosis/treatment support robot. With this, at least either one of the diagnosis or the treatment can be performed by using the surgical manipulator.

A diagnosis/treatment support robot system according to yet another aspect of the present disclosure includes: the above diagnosis/treatment support robot; a remote controller by which the operator remotely manipulates the surgical manipulator of the diagnosis/treatment support robot; and a first imager that is attached to the instrument mount of the robotic arm of the surgical manipulator and takes an image of a state of an area where the diagnosis/treatment for the target person is performed. The surgical manipulator includes a plurality of the robotic arms. The robotic arms includes: a diagnosis/treatment arm including the instrument mount to which the auxiliary instrument is attached; and an imaging arm including the instrument mount to which the first imager is attached. The remote controller includes: a second display that displays the image of the state of the area which is taken by the first imager; and a second imager that takes an image of the operator. The surgical manipulator further includes a first display that displays the image of the operator which is taken by the second imager.

According to this configuration, the first imager attached to the instrument mount of the robotic arm of the surgical manipulator can take the image of the state of the area (hereinafter referred to as a "diagnosis/treatment area") where the diagnosis/treatment for the target person is performed, and the taken image of the state of the diagnosis/treatment area can be displayed on the second display of the remote controller. With this, since the operator can manipulate the surgical manipulator while watching the state of the diagnosis/treatment area on the second display, the auxiliary practice of the diagnosis or the auxiliary practice of the treatment can be appropriately performed. Especially, since the first imager is attached to the robotic arm of the surgical manipulator, the operator can freely manipulate the first imager to watch what the operator wants to watch in such a manner that the operator wants to watch.

Moreover, the first display of the surgical manipulator can display the image of the operator taken by the second imager of the remote controller. Therefore, the target person can know the states (facial expressions, attitudes, etc.) of the operator. As a result, the target person can relax. As above, the operator and the target person can communicate with each other by the video image.

A diagnosis/treatment support method according to still another aspect of the present disclosure is a diagnosis/treatment support method using a diagnosis/treatment support robot. The diagnosis/treatment support robot includes a surgical manipulator that is remotely manipulated by an operator. The surgical manipulator includes a robotic arm. The robotic arm includes an instrument mount at a tip thereof. A surgical instrument for surgery of a patient is attached to the instrument mount. An auxiliary instrument is attachable to the instrument mount. The auxiliary instrument is an instrument other than the surgical instrument. The auxiliary instrument is an instrument for at least either one of an auxiliary practice of a diagnosis of an infectious disease for a target person or an auxiliary practice of a treatment of the infectious disease for the target person. The diagnosis/treatment support method includes attaching the auxiliary instrument instead of the surgical instrument to the instrument mount.

According to this configuration, the surgical manipulator can perform at least either one of the auxiliary practice of the diagnosis or the auxiliary practice of the treatment in place of the medical worker. With this, the medical worker can be prevented from being infected with the infectious disease.

Advantageous Effects of Invention

The present disclosure achieves an effect of being able to provide a diagnosis/treatment support robot, a diagnosis/treatment support robot system, and a diagnosis/treatment support method, each of which can perform at least either one of an auxiliary practice of a diagnosis or an auxiliary practice of a treatment in place of a medical worker, and with this, can prevent the medical worker from being infected with an infectious disease.

DESCRIPTION OF EMBODIMENTS

Embodiment

Figure 1:
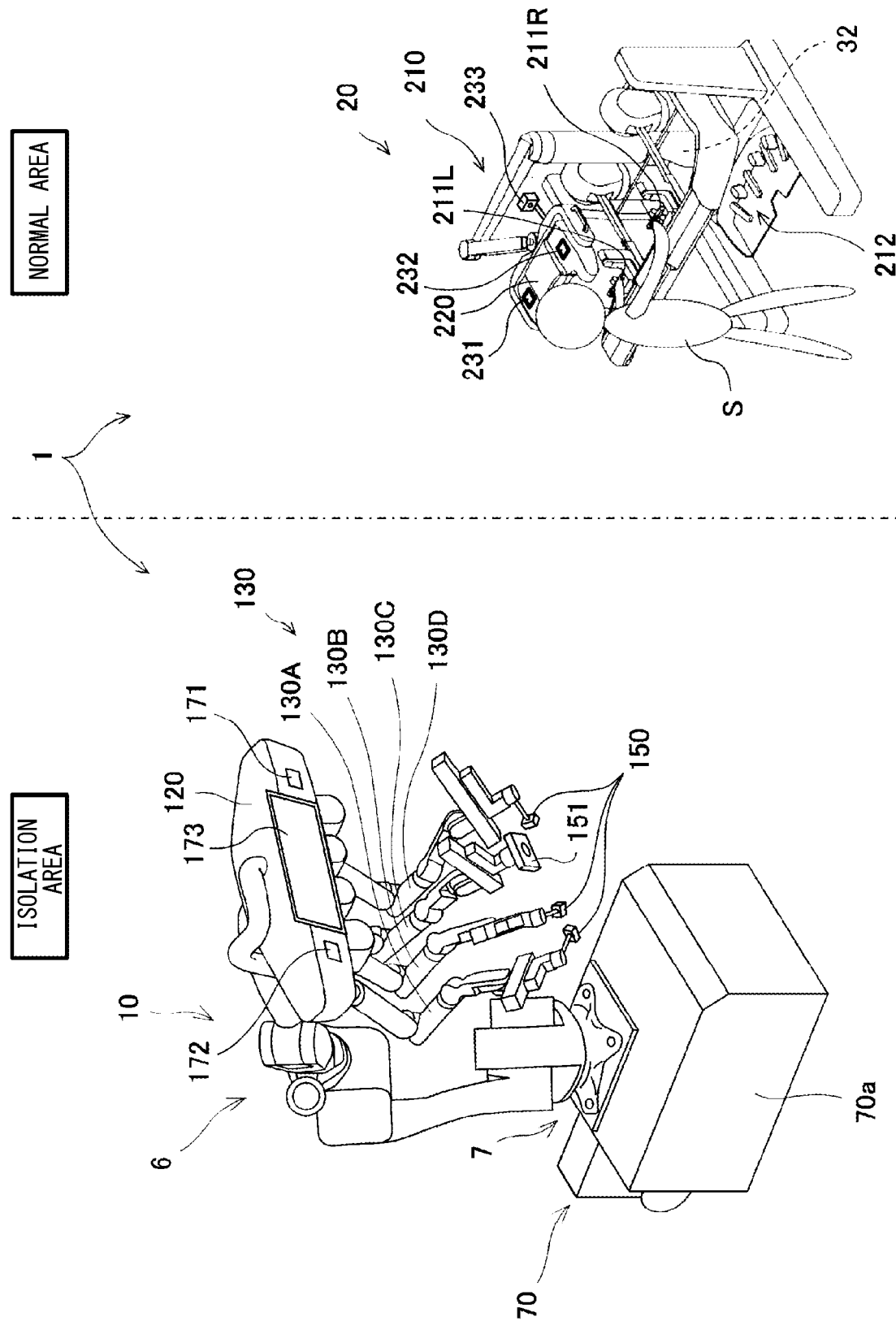
FIG. 1 is an external view showing one example of a hardware configuration of a diagnosis/treatment support robot system according to the present disclosure.

Hereinafter, a specific embodiment of the present disclosure will be described with reference to the drawings. In the following description and the drawings, the same reference signs are used for the same or corresponding components, and the repetition of the same explanation is avoided. The drawings described below are drawings for explaining the present disclosure. Therefore, for example, components not related to the present disclosure may be omitted in the drawings. Dimensions may not be accurate in the drawings due to exaggeration or the like. Corresponding components in the drawings may not coincide with each other. The present disclosure is not limited to the embodiment below.

Hardware Configuration

Figure 2:
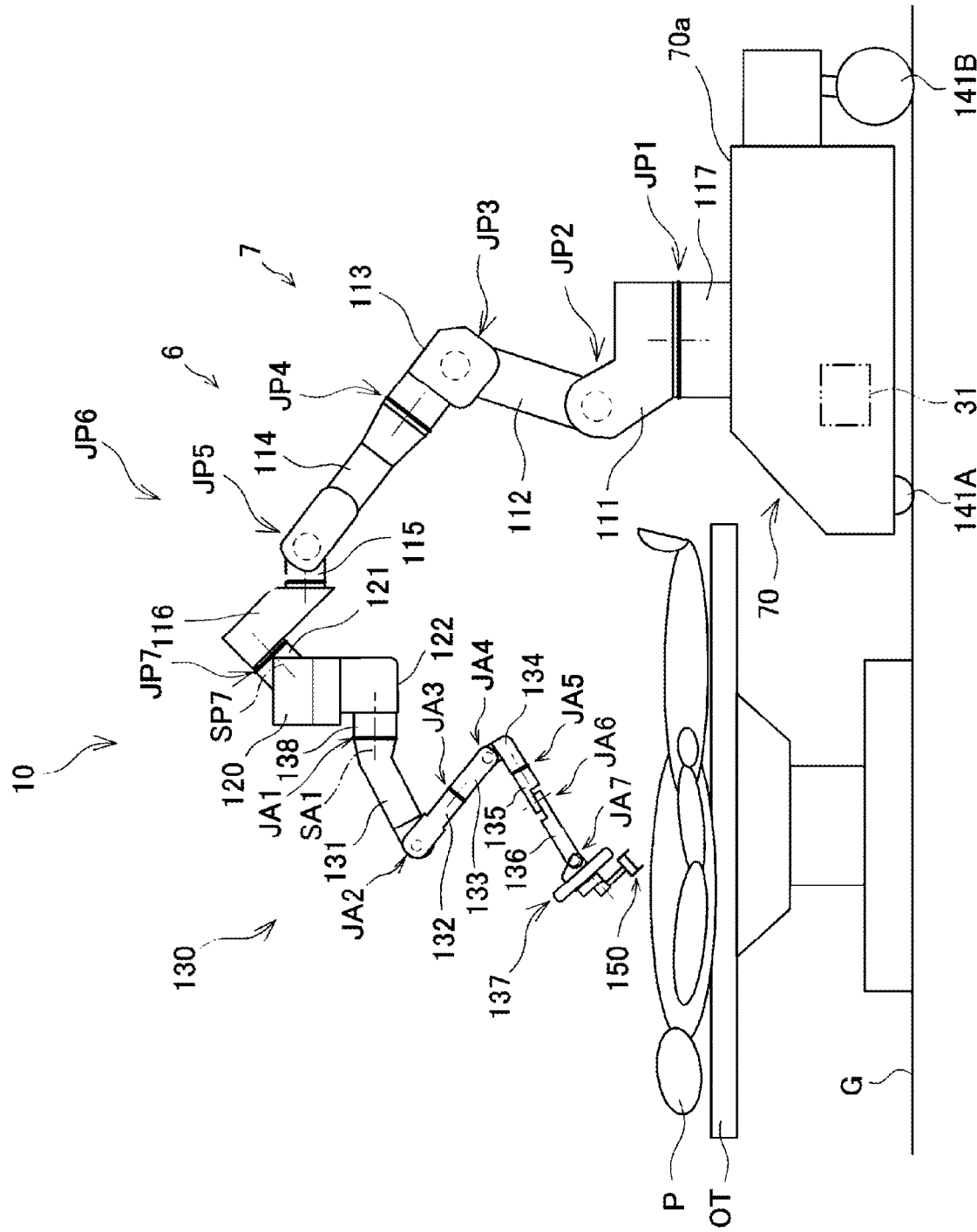
FIG. 2 is an external view showing one example of the configuration of a surgical manipulator of FIG. 1.

FIG. 1 is an external view showing one example of a hardware configuration of a diagnosis/treatment support robot system according to the present disclosure. FIG. 2 is an external view showing one example of the configuration of a surgical manipulator of FIG. 1. In FIG. 2, a display 173 of FIG. 1 is not shown.

As shown in FIG. 1, a diagnosis/treatment support robot system 1 of the present embodiment includes a diagnosis/treatment support robot 10 and a remote controller 20. The diagnosis/treatment support robot 10 is disposed in an isolation area where an infected person or a suspected infected person is isolated. The isolation area is, for example, a depressurized room. The remote controller 20 is disposed in a normal area that is not isolated.

Hereinafter, the configuration of the diagnosis/treatment support robot system will be described in detail.

Diagnosis/Treatment Support Robot 10

As shown in FIGS. 1 and 2, the diagnosis/treatment support robot 10 includes a surgical manipulator 6 and a cart 70.

Cart 70

The cart 70 includes a main body 70a, front wheels 141A, and a rear wheel 141b. The front wheels 141A are driving wheels, and the rear wheel is a steered wheel. The front wheels are driven by a driving source (not shown; for example, a motor) incorporated in the main body 70a. The rear wheel is steered by the driving source. With this, the cart 70 can autonomously travel. The main body 70a houses a first controller 31. The operations of the front wheels 141A and the rear wheel 141b are controlled by the first controller 31. With this, the cart 70 can automatically travel. The first controller 31 controls the operations of the front wheels 141A and the rear wheel 141b in accordance with a stored travel program or a travel command from the remote controller 20 as will be described later. Herein, the first controller 31 controls the front wheels 141A and the rear wheel 141b in accordance with the travel program. With this, the cart 70 moves from the normal area to the isolation area through a preset movement route.

Surgical Manipulator 6

The surgical manipulator 6 is not especially limited, and a known surgical manipulator may be used as the surgical manipulator 6. Herein, the surgical manipulator 6 includes a positioner 7 and robotic arms 130.

The positioner 7 positions the robotic arms 130 at positions where the robotic arms 130 easily perform work for a target person (a patient in the case of surgery; an infected person or a suspected infected person in the case of a diagnosis or a treatment).

Specifically, the positioner 7 includes a vertical articulated robot. Herein, the positioner 7 includes: first to sixth positioner links 111 to 116 arranged from a base 117 toward a tip of the positioner 7; and seven joints JP1 to JP7 coupling the first to sixth positioner links 111 to 116 in order. An arm base 120 is disposed at the tip of the positioner 7. The base 117 is fixed to an upper surface of the main body 70a of the cart 70.

The arm base 120 functions as a platform of the robotic arms 130. The robotic arms 130 are coupled to the arm base 120. The number of robotic arms 130 is not especially limited. Herein, the number of robotic arms 130 is four. When the robotic arms are collectively described or when a representative example of the robotic arms is described, a reference sign "130" is used. When the robotic arms are individually described (mentioned), the reference sign "130" to which a capital alphabetical letter is attached is used for each robotic arm. Herein, the surgical manipulator 6 includes first to fourth robotic arms 130A to 130D.

FIG. 2 shows one robotic arm 130 as a representative of the four robotic arms 130A to 130D. In FIG. 2, a reference sign G represents a floor surface in the isolation area. A reference sign OT represents a bed. A reference sign P represents a target person. FIG. 2 shows that: the diagnosis/treatment support robot 10 is at a position suitable for the diagnosis and/or the treatment of the target person P who lies on his/her back on the bed OT; and an auxiliary practice of the diagnosis and/or an auxiliary practice of the treatment for the target person P are about to be performed by the surgical manipulator 6.

As shown in FIG. 2, the arm base 120 is coupled to the sixth positioner link 116 through a first attaching portion 121 so as to be rotatable about a rotation axis SP1 of the twist rotary joint JP7. Moreover, each of the robotic arms 130 is coupled to the arm base 120 through a second attaching portion 122.

The robotic arm 130 includes an articulated robotic arm. Herein, the robotic arm 130 includes: first to sixth arm links 131 to 136 arranged from a base 138 toward a tip of the robotic arm 130; and seven joints JA1 to JA7 coupling the first to sixth arm links 131 to 136 in order. An instrument mount 137 is coupled to the tip of the robotic arm 130. The base 138 is coupled to the second attaching portion 122 of the arm base 120 so as to be rotatable about a predetermined twisting rotation axis SA1. The predetermined twisting rotation axis SA1 is set to intersect with the rotation axis SP1 of the twist rotary joint JP7 at a predetermined angle when viewed from a longitudinal direction of the arm base 120.

An auxiliary instrument 150 is attached to the instrument mount 137.

Instrument Mount 137

Figure 3:
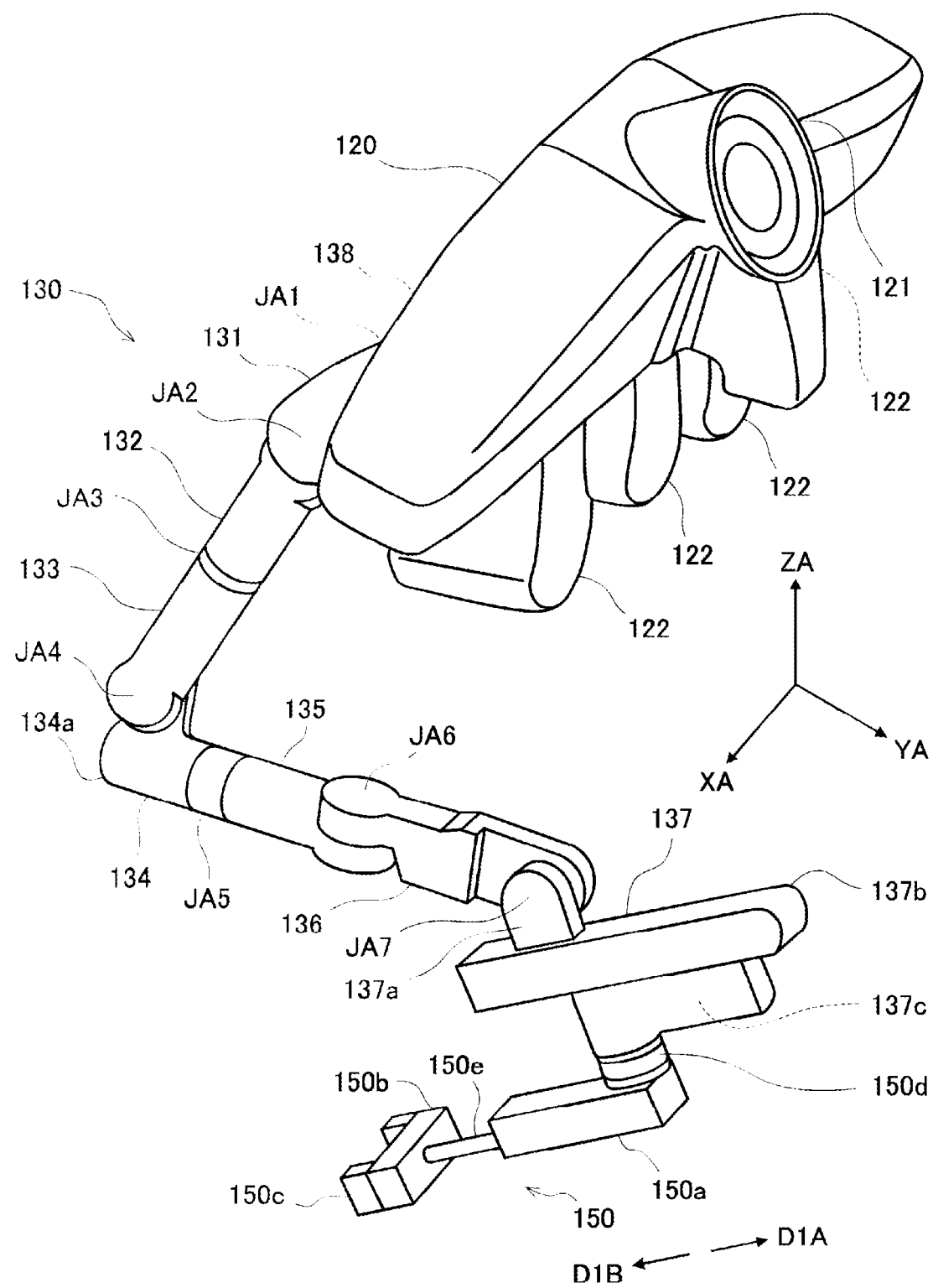
FIG. 3 is an external view showing one example of the configuration of a robotic arm of FIG. 2 and one example of the configuration of an auxiliary instrument.

FIG. 3 is an external view showing one example of the configuration of the robotic arm 130 of FIG. 2 and one example of the configuration of the auxiliary instrument 150 of FIG. 2. In FIG. 3, the display 173 of FIG. 1 is not shown.

As shown in FIG. 3, the robotic arm 130 can freely move the instrument mount 137 in three directions XA, YA, and ZA in three dimensions and can freely change the posture of the instrument mount 137 in the three directions XA, YA, and ZA in three dimensions.

The auxiliary instrument 150 has four (or more) degrees of freedom of movement of the auxiliary instrument 150. The auxiliary instrument 150 is attached to the instrument mount 137, and then the instrument mount 137 allows the auxiliary instrument 150 to operate in four (or more) degrees of freedom of movement thereof. Therefore, the auxiliary instrument 150 can perform complex work.

The instrument mount 137 includes an attaching portion 137a, a main body 137b, and a movable body 137c. The attaching portion 137a projects from one side of the main body 137b and is coupled to the sixth arm link 136 of the robotic arm 130 so as to be rotatable about a rotation axis (not shown) of the seventh joint JT7 that is a bending rotary joint. The main body 137b moves the movable body 137c in directions D1A and D1B orthogonal to the rotation axis of the seventh joint JT7. The auxiliary instrument 150 is coupled to the movable body 137c. Therefore, the instrument mount 137 moves the auxiliary instrument 150 in the directions D1A and D1B.

Figure 4:
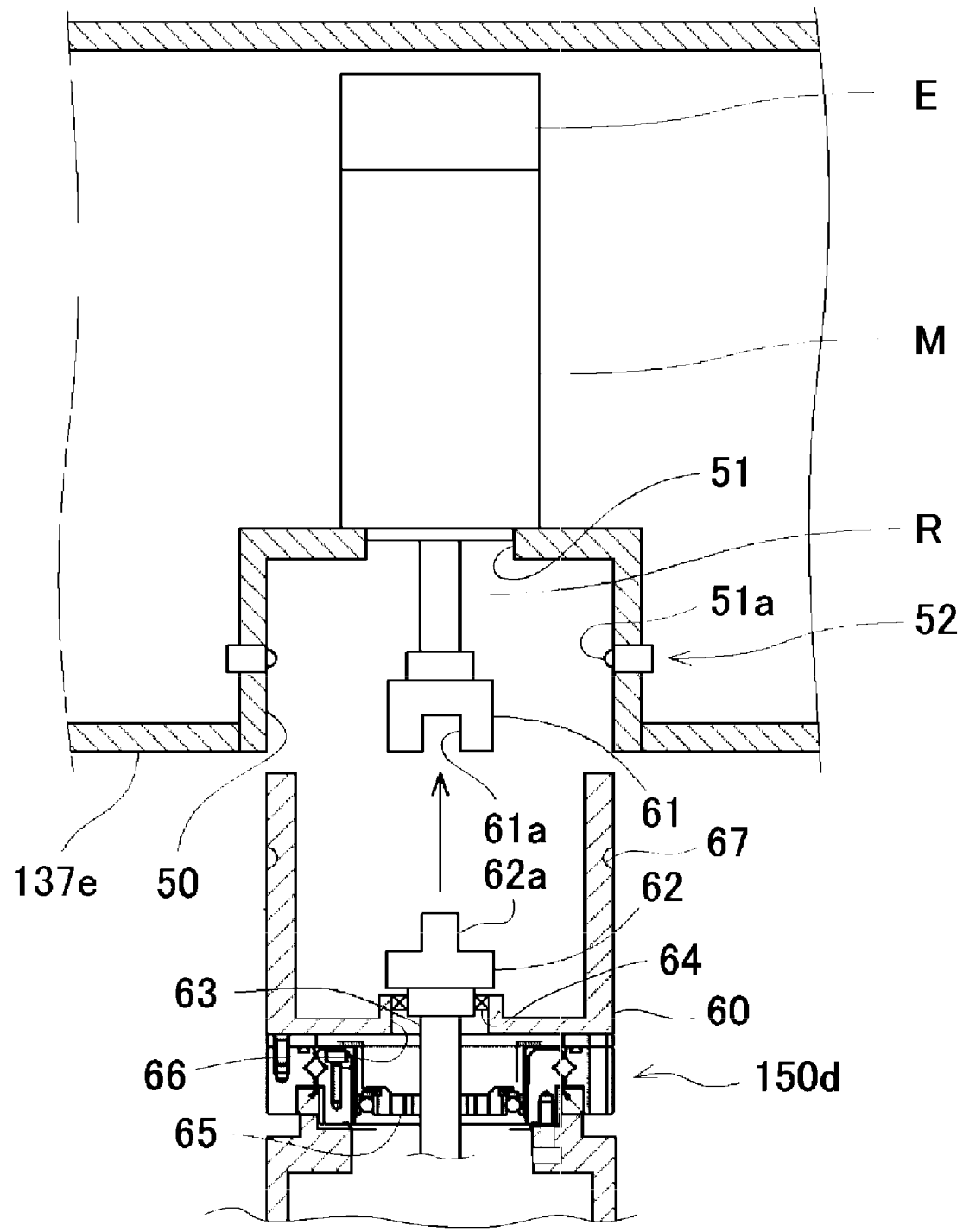
FIG. 4 is a sectional view showing one example of the configuration of a movable body of an instrument mount of FIG. 3.

FIG. 4 is a vertical sectional view showing one example of the configuration of the movable body 137c of the instrument mount 137 of FIG. 3. FIG. 4 shows a vertical section in a longitudinal direction of the movable body 137c of FIG. 3.

As shown in FIG. 4, the movable body 137c has a hollow box shape. A motor (for example, a servomotor) M and an encoder E as a rotation angle detector coupled to a main shaft R of the motor M are disposed in the movable body 137c. A cylindrical recess 50 is formed at one end of the movable body 137c on a side surface of the movable body 137c which is located at an opposite side of the main body 137b. A central axis of the recess 50 extends in a direction orthogonal to the rotation axis of the seventh joint JT7 and the directions D1A and D1B. An opening 51 is formed in the middle of a bottom surface of the recess 50. The motor M and the encoder E are disposed such that the main shaft R projects through the opening 51 to an outside. The motor M is arranged such that the main shaft R coincides with the central axis of the recess 50. A female coupling 61 is disposed at a tip of the main shaft R. A fitting recess 61*a* having a distinct cross-sectional shape is formed on a tip surface of the female coupling 61. Examples of the distinct cross-sectional shape include a minus shape, a plus shape, a square shape, and a hexagonal shape.

Locks 52 are disposed at at least one pair of opposing portions on an inner peripheral surface of the recess 50. Each of the locks 52 includes a locking pin 51*a* that can protrude or retract in a radial direction of the recess 50. A tip of the locking pin 51*a* has a semi-spherical shape. The locking pin 51*a* is biased in the radial direction of the recess 50 by an elastic structure (not shown).

On the other hand, as will be described later, the auxiliary instrument 150 includes an attaching portion 150*d*, and the attaching portion 150*d* includes a cylindrical projection 60 whose tip is open. The projection 60 has a shape that is fitted into the recess 50. Therefore, a central axis of the projection 60 coincides with the central axis of the recess 50. An opening 66 is formed in the middle of a bottom surface of the projection 60. A driving shaft 63 is disposed so as to extend from an inside of the projection 60 through the opening 66 to an inside of the attaching portion 150*d*. The driving shaft 63 is rotatably supported by a bearing 64 disposed in at the opening 66 such that a rotation axis of the driving shaft 63 coincides with a rotation axis of the main shaft R of the motor M. A male coupling 62 is disposed at a tip of the driving shaft 63. A fitting projection 62*a* fitted into the fitting recess 61*a* of the female coupling 61 is formed on a tip surface of the male coupling 62. The male coupling 62 is located such that when the projection 60 is fittingly inserted deep into the recess 50, the fitting projection 62*a* is inserted and just fitted into the fitting recess 61*a* of the female coupling 61.

Engagers 67 are disposed at at least one pair of portions on an outer periphery of the projection 60, the pair of portions facing in directions opposite to each other. Each of the engagers 67 is a recess that is recessed in a radial direction of the projection 60 in a semi-spherical shape. The engagers 67 are located such that when the projection 60 is fittingly inserted deep into the recess 50, the locking pins 51*a* of the recess 50 just protrude into the engagers 67, and thus, the projection 60 is locked to the recess 50. A reference sign 65 represents a seal structure that seals an inside of the attaching portion 150*d*.

When attaching the auxiliary instrument 150 to the movable body 137*c* (instrument mount 137), the projection 60 of the auxiliary instrument 150 is pushed deep into the recess 50 of the movable body 137*c*. With this, the locking pins 51*a* in the recess 50 protrude toward (enter into) the engagers 67 of the projection 60 to lock the projection 60 to the recess 50. Thus, the auxiliary instrument 150 is attached to the movable body 137*c*.

In this state, when the projection 60 is pulled by required force in such a direction that the projection 60 is pulled out from the recess 50, the auxiliary instrument 150 is pulled out from the movable body 137*c*. Thus, the auxiliary instrument 150 is detached from the movable body 137*c*.

As will be described later, rotational power of the driving shaft 63 is transmitted to a claw holding body 150*b* of the auxiliary instrument 150 through a suitable power transmitting structure.

When attaching an imager 151 (see FIG. 1) to the movable body 137*c*, the projection 60 is attached to the imager 151. Moreover, the female coupling 61 of the recess 50 and the male coupling 62 of the projection 60 are omitted, and instead of these, electric contacts through which control signals, data, and the like of the imager 151 are transmitted are disposed at the recess 50 and the projection 60.

When attaching a surgical instrument 180 (see FIG. 8) to the movable body 137*c*, the recess 50 and the projection 60 are configured in accordance with the type of the surgical instrument 180.

When the surgical instrument 180 includes a drive portion driven by the motor M, the recess 50 and the projection 60 are configured in the same manner as above.

When the surgical instrument 180 does not include the drive portion driven by the motor M but requires the transmission of electric power, control signals, data, and the like, the female coupling 61 of the recess 50 and the male coupling 62 of the projection 60 are omitted, and instead of these, electric contacts through which electric power, control signals, data, and the like are transmitted are disposed at the recess 50 and the projection 60.

When the surgical instrument 180 does not include the drive portion driven by the motor M and does not require the transmission of electric power, control signals, data, and the like, the female coupling 61 of the recess 50 and the male coupling 62 of the projection 60 are omitted.

Attaching and detaching of the surgical instrument 180 to and from the movable body 137*c* are the same as those of the auxiliary instrument 150 in the above case.

Auxiliary Instrument 150

As shown in FIG. 1, the auxiliary instruments 150 are attached to a tip of the first robotic arm 130A, a tip of the second robotic arm 130B, and a tip of the fourth robotic arm 130D.

Regarding industrial robots, there are various types of hands (end effectors) that can appropriately handle or process various types of members. Therefore, various types of auxiliary instruments 150 that can appropriately handle or process various types of members can be obtained by suitably modifying various types of hands.

Especially, in the auxiliary practice of the diagnosis or the auxiliary practice of the treatment, a medical worker holds a diagnosis/treatment tool with his/her hands in many cases. A holding instrument as one example of the auxiliary instrument 150 is a tool attached to the tip of the robotic arm 130 in order that the holding instrument holds the diagnosis/treatment tool to widely perform the auxiliary practice of the diagnosis or the auxiliary practice of the treatment in place of the medical worker.

Examples of the diagnosis/treatment tool include: a tool that collects a specimen regarding an infectious disease of the target person P; a drip infusion tool; a blood collecting tool; and a cannula of an artificial heart and lung apparatus.

As in the present embodiment, when the auxiliary instrument 150 (especially, the holding instrument) that can hold the diagnosis/treatment tool is put into practical use (is made available), practices especially necessary for the diagnosis of the infectious disease or the treatment of the infectious disease can be performed by using the surgical manipulator 6. In the following, as one example, the holding instrument holds the diagnosis/treatment tool. However, the holding instrument may hold the diagnosis/treatment tool by reduced pressure.

Moreover, instead of holding the diagnosis/treatment tool, the auxiliary instrument 150 may be a tool (such as a cutting tool, a nozzle, or a placing tool), a processing tool, or a conveying tool.

As shown in FIG. 3, the auxiliary instrument 150 includes, for example, a main body 150*a*, the claw holding body 150*b*, a pair of claws 150*c*, the attaching portion 150*d*, and a coupler 150*e*.

For example, the claw holding body 150*b* linearly moves the pair of claws 150*c* in a predetermined direction to open or close the pair of claws 150*c*. Examples of the structure of the claw holding body 150*b* include a rack and pinion structure and a ball screw structure. The shape of each of the pair of claws 150*c* is not especially limited and is a flat plate shape herein. Each of the pair of claws 150*c* is a rigid body made of metal, plastic, or the like, and a cushion layer (not shown) is disposed on an inner surface of each claw 150*c*. The cushion layer has suitable properties, such as thickness, elasticity, and friction coefficient. These properties are selected in accordance with the diagnosis/treatment tool that is a target to be held. These selections are decided by experiments, simulations, calculations, and the like.

The claw holding body 150*b* is coupled to the main body 150*a* through the coupler 150*e* that is hollow. As described above, the attaching portion 150*d* projects from an appropriate portion of the main body 150*a*. A power transmission path structure, through which the rotational power of the driving shaft 63 is transmitted as the driving power of the pair of claws 150*c*, extends from the attaching portion 150*d* through an inside of the main body 150*a* and an inside of the coupler 150*e* to the claw holding body 150*b*. Since such power transmission path structure can be realized by a known technology, the explanation thereof is omitted.

Therefore, the pair of claws 150*c* are driven by the motor M located at the movable body 137*c*.

Hold Facilitating Jig

Some of the diagnosis/treatment tools are difficult for the holding instrument to directly hold them. Examples of such tools include: fragile tools (syringes, containers, and the like made of glass); too thin or too small tools (thin tubes and the like); and tools that are difficult to be held since the shapes thereof are complex. In this case, a jig that is easy for the holding instrument to hold is attached to such diagnosis/treatment tool in advance. With this, the holding instrument holds the jig, and as a result, the holding instrument can easily hold the diagnosis/treatment tool.

Figure 5:
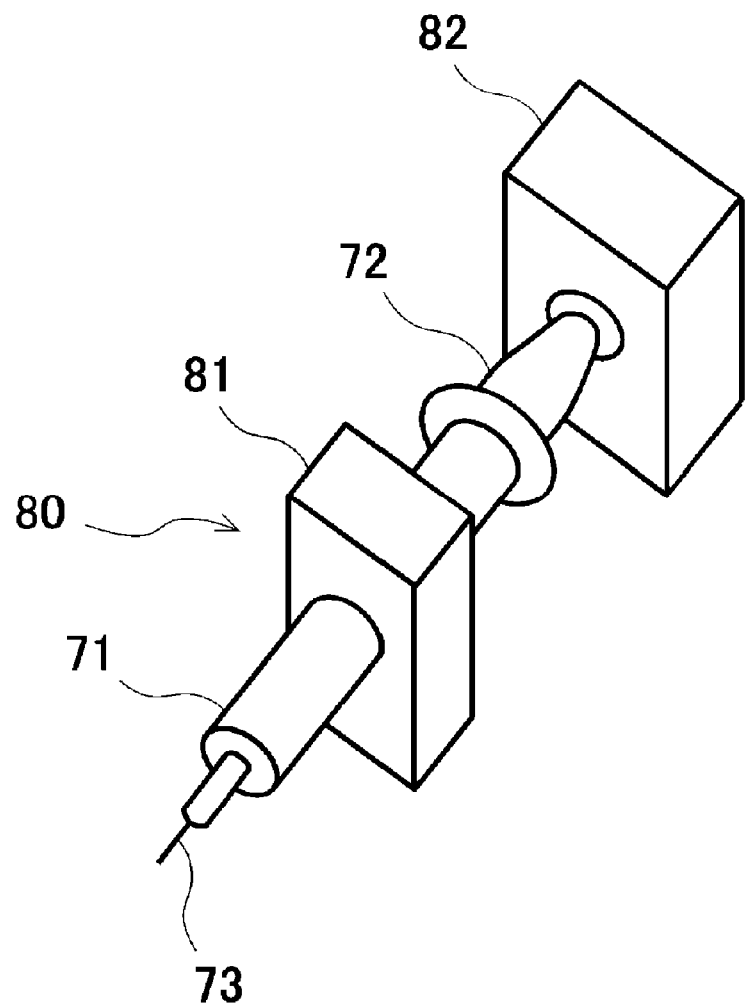
FIG. 5 is an external view showing a syringe to which hold facilitating jigs are attached.

FIG. 5 is an external view showing a syringe 80 to which hold facilitating jigs 81 and 82 are attached. As shown in FIG. 5, the syringe 80 includes a cylinder 71, a piston 72, and an injection needle 73. The first hold facilitating jig 81 is attached to the cylinder 71, and the second hold facilitating jig 82 is attached to the piston 72. The first hold facilitating jig 81 has a rectangular solid shape and includes a circular through hole in the middle of the first hold facilitating jig 81. The cylinder 71 is inserted through the through hole, and the first hold facilitating jig 81 is firmly fixed to the cylinder 71 by a suitable adhesive. The second hold facilitating jig 82 has a rectangular solid shape and includes a circular recess in the middle of one side surface of the second hold facilitating jig 82. A rear end of the piston 72 is fittingly inserted into the recess, and the second hold facilitating jig 82 is firmly fixed to the piston 72 by a suitable adhesive.

For example, when colleting blood, the auxiliary instrument 150 of the first robotic arm 130A (diagnosis/treatment arm) holds the first hold facilitating jig 81, and the auxiliary instrument 150 of the second robotic arm 130B (diagnosis/treatment arm) holds the second hold facilitating jig 82. Then, an operator manipulates the first robotic arm A and the second robotic arm 130B with his/her left and right hands. Thus, the blood is collected by the syringe 80.

Remote Controller 20

As shown in FIG. 1, the remote controller 20 includes a manipulation inputter 210, a display 220, and a second controller 32. The remote controller 20 further includes a second speaker 231, a second microphone 232, and a second imager 233.

The manipulation inputter 210 includes left and right operation manipulators 211L and 211R and manipulating pedals 212. The operation manipulators 211L and 211R are used to input the positions and postures of the auxiliary instruments 150 and the first imager 151 of the surgical manipulator 6. The manipulating pedals 212 are used to input commands regarding zoom-in and zoom-out of the first imager 151, switching of a control mode, and switching of the robotic arms 130 associated with the operation manipulators 211L and 211R.

The second controller 32 transmits to the first controller 31 of the diagnosis/treatment support robot 10, data (signal) which is input by the operation manipulators 211L and 211R and relates to the positions and postures of the auxiliary instruments 150 and the first imager 151 of the surgical manipulator 6. The second controller 32 transmits to the first controller 31, commands and the like input by the manipulating pedals 212. The second controller 32 performs display control of the display 220 and required control regarding the second speaker 231, the second microphone 232, and the second imager 233.

In the present embodiment, the robotic arms 130 of the surgical manipulator 6 are controlled by the operation manipulators 211L and 211R in a master-slave mode. However, the master-slave mode does not have to be used.

Communication Tool Using Sounds

As shown in FIGS. 1 and 2, as a communication tool using sounds between an operator (medical worker) S and the target person P, a first speaker 171 and a first microphone 172 are disposed on a front surface of the arm base 120 of the surgical manipulator 6. The first speaker 171 transmits to the target person P, voice of the operator S which is acquired by the second microphone 232 of the remote controller 20. The first microphone 172 acquires voice of the target person P.

On the other hand, the remote controller 20 includes the second speaker 231 and the second microphone 232. The second speaker 231 transmits to the operator S the voice of the target person P which is acquired by the first microphone 172. The second microphone 232 acquires the voice of the operator S.

Communication Tool Using Video Image

As shown in FIGS. 1 and 2, as a communication tool using a video image between the operator S and the target person P, the display (first display) 173 is disposed on the front surface of the arm base 120 of the surgical manipulator 6, and the first imager 151 is attached to the instrument mount 170 (specifically, the movable body 137*c*) of the third robotic arm 130C (imaging arm).

On the other hand, the remote controller 20 includes: the display 220 (second display) that displays an image of a state of a diagnosis/treatment area which is taken by the first imager 151; and a second imager 223 that takes an image of the operator S. For example, each of the first and second imagers 151 and 233 includes a camera, an image sensor, and the like. For example, each of the displays 173 and 220 includes a liquid crystal display and the like.

According to this configuration, the first imager 151 of the surgical manipulator 6 can take the image of the state of the diagnosis/treatment area where the diagnosis/treatment for the target person P is performed, and the taken image of the state of the diagnosis/treatment area can be displayed on the display 220 of the remote controller 20. With this, since the operator S can manipulate the surgical manipulator 6 while watching the state of the diagnosis/treatment area on the display 220, the auxiliary practice of the diagnosis or the auxiliary practice of the treatment can be appropriately performed. Since the first display of the surgical manipulator displays the image of the operator S which is taken by the second imager 233 of the remote controller 20, the target person P can know the states of the operator S. Therefore, the operator S and the target person P can communicate with each other by the video image.

Configuration of Control System

Figure 6:
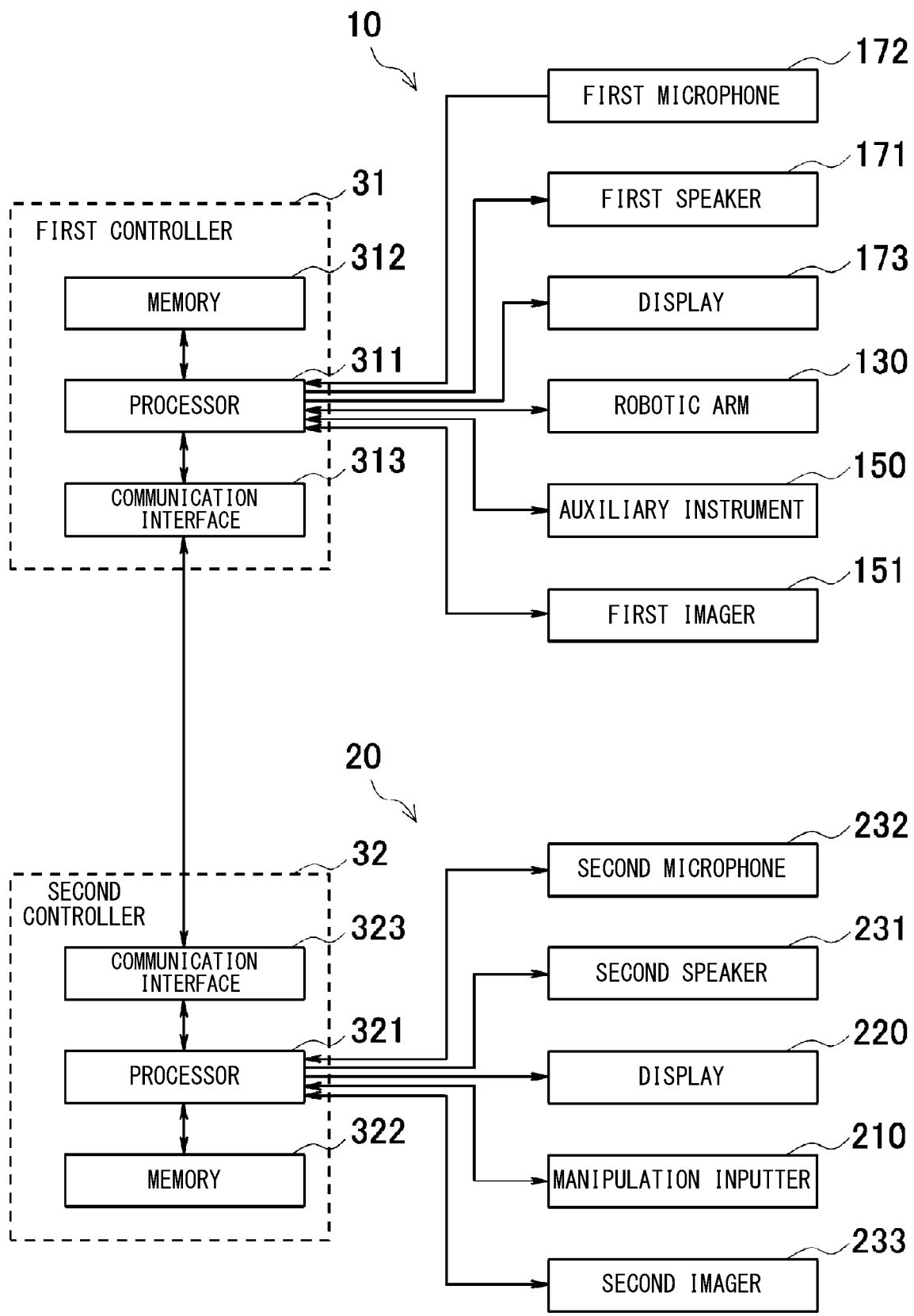
FIG. 6 is a block diagram showing one example of the configuration of a control system of the diagnosis/treatment support robot system of FIG. 1.

FIG. 6 is a block diagram showing one example of the configuration of a control system of the diagnosis/treatment support robot system 1 of FIG. 1.

As shown in FIG. 6, the first controller 31 includes a processor 311, a memory 312, and a communication interface 313. Examples of the processor 311 include a CPU, a MPU, a FPGA (Field Programmable Gate Array), and a PLC (Programmable Logic Controller). Examples of the memory 312 include a ROM, a RAM, and an external storage device (for example, a SSD (Solid State Drive) and a hard disc drive). Examples of the communication interface 313 include a modem, an ONU (Optical Network Unit), and a router.

The first controller 31 performs required control, processing, and the like in such a manner that the processor 311 executes a control program stored in the memory 312.

The robotic arms 130, the auxiliary instruments 150, the first imager 151, the first speaker 171, the first microphone 172, and the display 173 are connected to the processor 311.

The second controller 32 includes a processor 321, a memory 322, and a communication interface 323. Examples of the processor 321 include a CPU, a MPU, a FPGA (Field Programmable Gate Array), and a PLC (Programmable Logic Controller). Examples of the memory 322 include a ROM, a RAM, and an external storage device (for example, a SSD (Solid State Drive) or a hard disc drive). Examples of the communication interface 323 include a modem, an ONU (Optical Network Unit), and a router.

The second controller 32 performs required control, processing, and the like in such a manner that the processor 321 executes a control program stored in the memory 322.

The communication interface 313 and the communication interface 323 are connected to each other so as to be able to perform data communication. Examples of the data communication include wired communication, wireless communication, and optical communication.

Functionality of Elements Disclosed in Present Description

The functionality of the elements disclosed herein may be implemented using circuitry or processing circuitry which includes general purpose processors, special purpose processors, integrated circuits, ASICs ("Application Specific Integrated Circuits"), conventional circuitry and/or combinations thereof which are configured or programmed to perform the disclosed functionality. Processors are considered processing circuitry or circuitry as they include transistors and other circuitry therein. In the disclosure, the devices, units, or portions are hardware that carry out or are programmed to perform the recited functionality. The hardware may be any hardware disclosed herein or otherwise known which is programmed or configured to carry out the recited functionality. When the hardware is a processor which may be considered a type of circuitry, the devices, units, or portions are a combination of hardware and software, the software being used to configure the hardware and/or processor.

Auxiliary Robot

Figure 7:
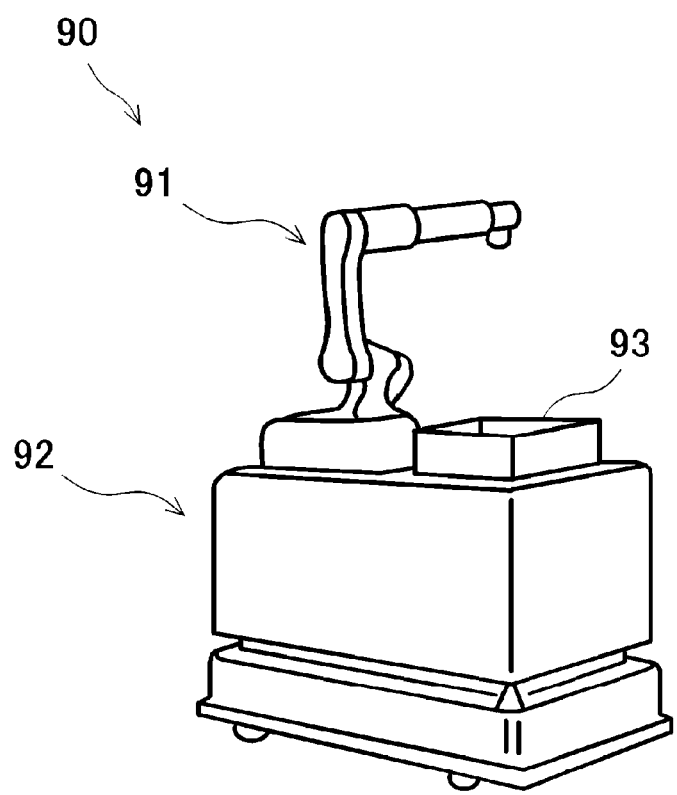
FIG. 7 is an external view showing one example of the configuration of an auxiliary robot.

FIG. 7 is an external view showing one example of the configuration of an auxiliary robot 90. The auxiliary robot 90 includes a cart 92 and a robotic arm 91 disposed on the cart 92. The cart 92 can autonomously travel. For example, the robotic arm 91 includes an articulated robotic arm.

The auxiliary robot 90 is manipulated by an operator different from the operator S of the diagnosis/treatment support robot 10 and moves between the normal area and the isolation area while carrying thereon a storage box 93 that houses items (the diagnosis/treatment tools, medicines, and the like) necessary for the auxiliary practice of the diagnosis and the auxiliary practice of the treatment. When the auxiliary robot 90 moves as above, the auxiliary robot 90 performs required disinfection by itself.

Then, the auxiliary robot 90 assists the auxiliary practice of the diagnosis or the auxiliary practice of the treatment which is performed by the diagnosis/treatment support robot 10. For example, the auxiliary robot 90 hands over the diagnosis/treatment tool to the surgical manipulator 6 such that the auxiliary instrument 150 of the surgical manipulator 6 can easily hold the diagnosis/treatment tool.

Operations

Next, examples of the operations of the above diagnosis/treatment support robot system 1 will be described.

Movement to Diagnosis/Treatment Area

As shown in FIG. 1, the remote controller 20 is disposed in the normal area. On the other hand, the diagnosis/treatment support robot 10 is normally disposed in the normal area. Then, the operator S manipulates a predetermined operating element (not shown) of the manipulation inputter 210 of the remote controller 20. With this, the diagnosis/treatment support robot 10 moves through the preset movement route to the diagnosis/treatment area in the isolation area. A disinfector is disposed at a portion of the movement route of the diagnosis/treatment support robot 10, and the diagnosis/treatment support robot 10 is disinfected by the disinfector. Examples of the disinfector include an alcohol spray and an ozone sterilizer. A spray container containing a disinfectant solution may be disposed at a portion of the movement route, and the diagnosis/treatment support robot 10 may be manipulated by the operator S to hold the spray container and spray the disinfectant solution to itself for disinfection.

Replacement of Instrument

Figure 8:
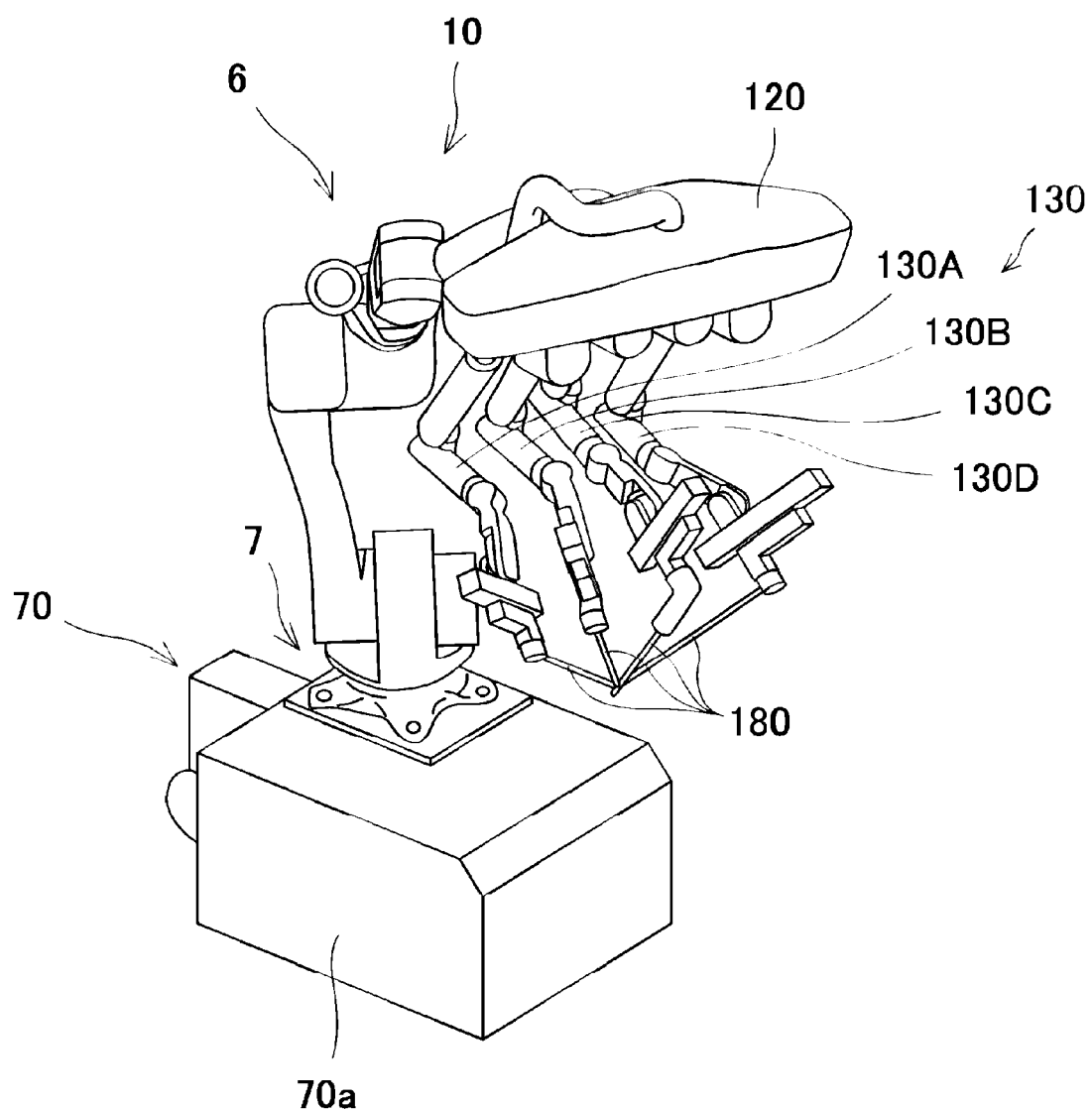
FIG. 8 is an external view showing the diagnosis/treatment support robot to which a surgical instrument is attached.

FIG. 8 is an external view showing the diagnosis/treatment support robot 10 to which the surgical instruments 181 are attached. In FIG. 8, the first speaker 171, the first microphone 172, the display 173, and the like of FIG. 1 are not shown.

As shown in FIG. 8, the operator S detaches the surgical instruments 180 from the diagnosis/treatment support robot 10. Then, as shown in FIG. 1, the operator S attaches the auxiliary instruments 150 and the first imager 151 to the diagnosis/treatment support robot 10.

Collection of Specimen

In this case, the auxiliary robot 90 of FIG. 7 is located beside the diagnosis/treatment support robot 10 and suitably assists the work of the diagnosis/treatment support robot 10 by another operator. The same is true in the other auxiliary practice of the diagnosis and the other auxiliary practice of the treatment.

As shown in FIGS. 1, 2, and 7, the operator S manipulates the manipulation inputter 210 of the remote controller 20 to cause the auxiliary instrument 150 (herein, the holding instrument) of the first robotic arm 130A of the surgical manipulator 6 to hold a swab, insert the swab into the back of the throat of the target person P, collect a swab fluid, and then put the swab into a predetermined container. After that, the auxiliary robot 90 puts the predetermined container into the housing box 93. In this process, the operator S manipulates the first imager 151 by using the third robotic arm 130C so as to be able to easily watch the face of the target person P on the display 220. The operator S provides necessary explanations, instructions, and the like to the target person P through the second microphone 232. On the other hand, the target person P follows the instructions of the operator S while watching the face of the operator S on the display 173 and listening to the voice of the operator S through the second microphone 232. Thus, the specimen is collected.

Blood Collection

As shown in FIGS. 1, 2, 5, and 7, the operator S manipulates the manipulation inputter 210 of the remote controller 20 so that the auxiliary instrument 150 (holding instrument) of the first robotic arm 130A of the surgical manipulator 6 holds the first hold facilitating jig 81 of the syringe 80 and the auxiliary instrument 150 (holding instrument) of the second robotic arm 130B of the surgical manipulator 6 holds the second hold facilitating jig 82 of the syringe 80. In this case, the piston 72 is inserted all the way into the cylinder 71 of the syringe 80.

Next, the operator S manipulates it to insert the injection needle 73 of the syringe 80 into a predetermined part of an arm of the target person P. In this process, the operator S manipulates the first imager 151 by using the third robotic arm 130C so as to be able to easily watch the arm of the target person P on the display 220. Moreover, the operator S provides necessary explanations, instructions, and the like to the target person P through the second microphone 232. On the other hand, the target person P follows the instructions of the operator S while watching the face of the operator S on the display 173 and listening to the voice of the operator S through the second microphone 232.

Next, the operator S manipulates it to slowly pull back the piston 72 with the cylinder 71 stationary. The operator S manipulates it to, when the amount of blood in the cylinder 71 of the syringe 80 on the display 220 reaches a predetermined amount, to pull out the syringe 80 from the arm of the target person P. Then, suitable processing is performed together with the auxiliary robot 90. Thus, the blood is collected.

Drip Infusion

As shown in FIGS. 1, 2, and 7, the operator S manipulates the manipulation inputter 210 of the remote controller 20 to cause the auxiliary instrument 150 (holding instrument) of the first robotic arm 130A to hold a container containing a drip infusion liquid and suspend the container from a predetermined suspending place. Then, the operator S manipulates it to cause the auxiliary instrument 150 (holding instrument) of the second robotic arm 130B to insert a needle at a tip of a tube for the drip infusion into a predetermined part (for example, the arm) of the target person P. In this process, the operator S manipulates the first imager 151 by using the third robotic arm 130C so as to be able to easily watch the predetermined part of the target person P on the display 220. The operator S provides necessary explanations, instructions, and the like to the target person P through the second microphone 232. On the other hand, the target person P follows the instructions of the operator S while watching the face of the operator S on the display 173 and listening to the voice of the operator S through the second microphone 232. Thus, the drip infusion work is performed.

Insertion of Cannula of Artificial Heart and Lung Apparatus

As shown in FIGS. 1, 2, and 7, the operator S manipulates the manipulation inputter 210 of the remote controller 20 to cause the auxiliary instrument 150 (holding instrument) of the first robotic arm 130A of the surgical manipulator 6 and the auxiliary instrument 150 (holding instrument) of the second robotic arm 130B of the surgical manipulator 6 to hold the cannula of the artificial heart and lung apparatus at a suitable distance from each other. Then, the operator S manipulates it to cause both of the robotic arms 130A and 130B to slowly insert the cannula into a blood vessel (the main artery or the main vein) at a predetermined part (for example, the root of the lower limb) of the target person P. In this process, the operator S manipulates the first imager 151 by using the third robotic arm 130C so as to be able to easily watch the predetermined part of the target person P on the display 220. Thus, the cannula is inserted.

Effects

As described above, according to the present embodiment, the diagnosis/treatment support robot system 1 performs at least either one of the auxiliary practice of the diagnosis or the auxiliary practice of the treatment in place of the medical worker, and with this, the medical worker can be prevented from being infected with the infectious disease.

Application Example to PCR Test

The present application example is one example in which the diagnosis/treatment support robot system 1 of the above embodiment is applied to the collection of the specimen of a PCR test for the infectious disease (for example, novel coronavirus (COVID-19)).

Figure 9:
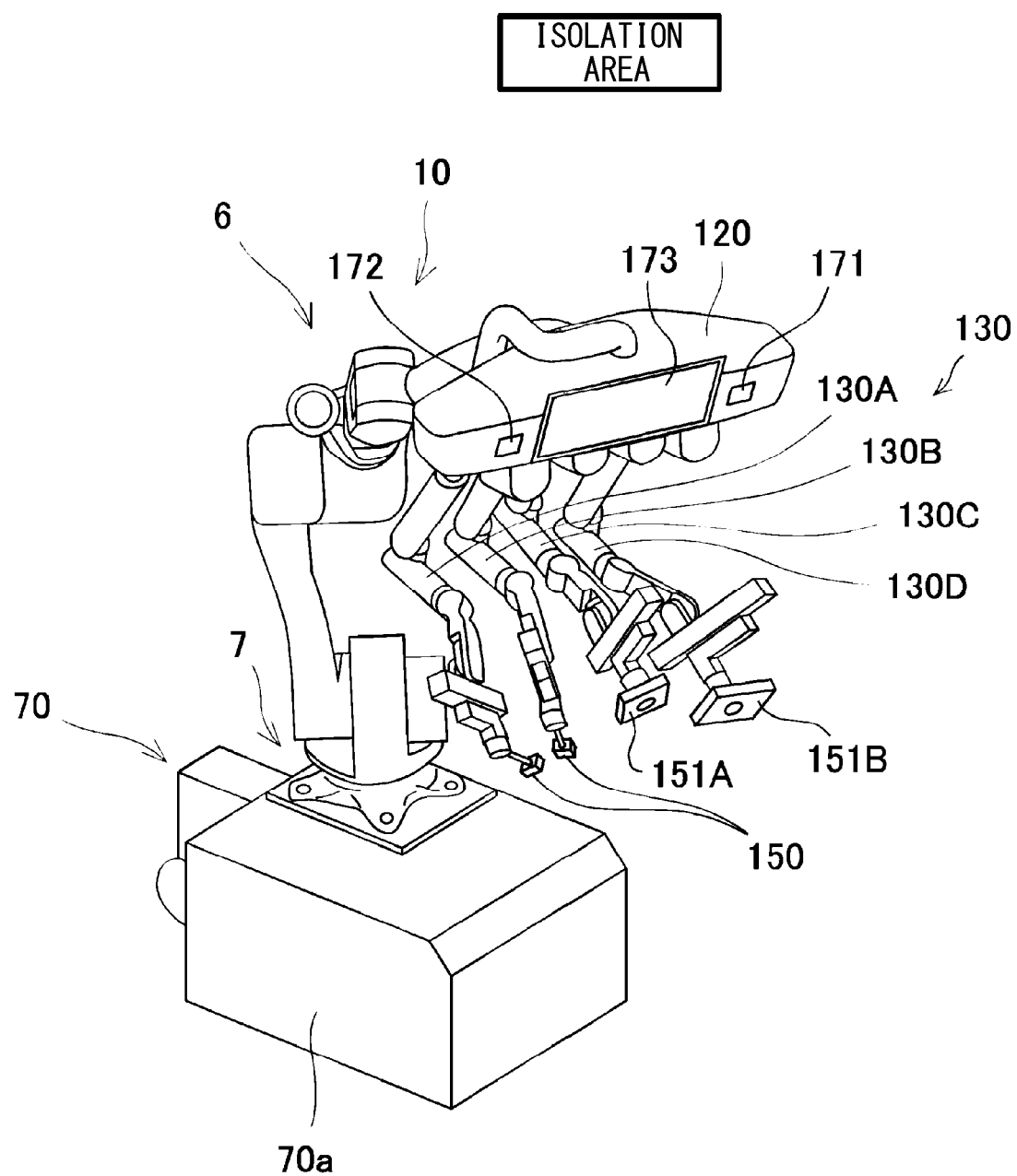
FIG. 9 is an external view showing one example of the configuration of the surgical manipulator of the diagnosis/treatment support robot system according to an application example of the present disclosure which is applied to a PCR test.

FIG. 9 is an external view showing one example of the configuration of the diagnosis/treatment support robot 10 of the diagnosis/treatment support robot system 1 according to the application example of the present disclosure which is applied to the PCR test.

Figure 10:
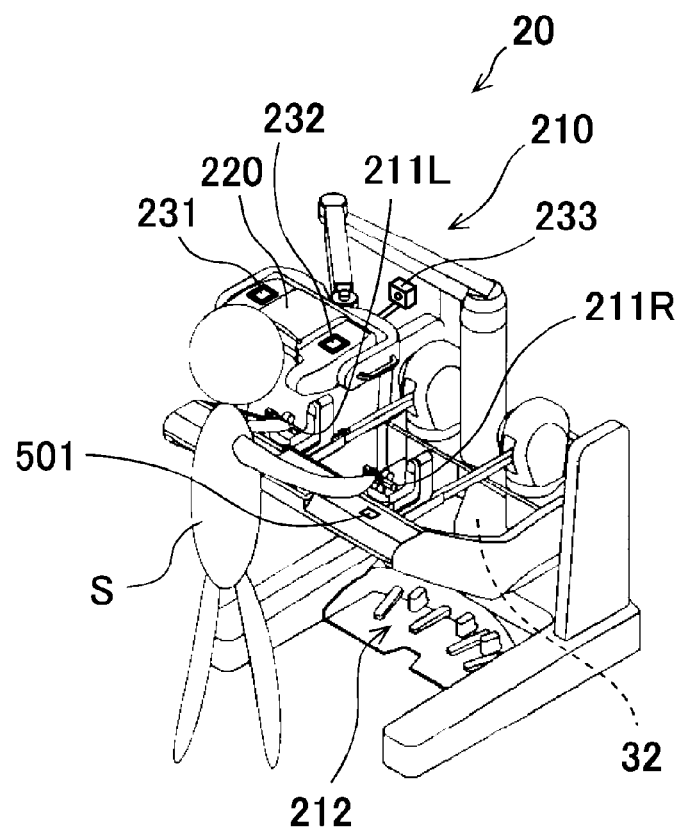
FIG. 10 is an external view showing one example of the configuration of a remote controller of the diagnosis/treatment support robot system according to the application example of the present disclosure which is applied to the PCR test.

As shown in FIGS. 9 and 10, the diagnosis/treatment support robot 10 of the diagnosis/treatment support robot system 1 is disposed in the isolation area, and the remote controller 20 of the diagnosis/treatment support robot system 1 is disposed in the normal area. With this, the operator can be prevented from being infected with the infectious disease.

As shown in FIG. 9, in the present application example, instead of the auxiliary instrument 150, the auxiliary imager 151B is attached to the fourth robotic arm 130D of the diagnosis/treatment support robot 10. Hereinafter, the first imager attached to the third robotic arm 130C is represented by a reference sign 151A and is distinguished from the auxiliary imager 151B. Each of the first imager 151A and the auxiliary imager 151B may be a video camera that can take a moving image or an X-ray camera. The auxiliary imager 151B may be held by the auxiliary robot as shown in FIG. 7 or may be disposed on a wall of the isolation area. One of the auxiliary instrument 150 attached to the first robotic arm 130A and the auxiliary instrument 150 attached to the second robotic arm 130B is a holding instrument 150 shown in FIG. 11. Herein, for example, the auxiliary instrument 150 attached to the first robotic arm 130A is the holding instrument 150 shown in FIG. 11. Hereinafter, for convenience sake, the third robotic arm is referred to as a "first imaging arm," the fourth robotic arm 130D is referred to as an "auxiliary imaging arm," and the robotic arm to which the holding instrument 150 of FIG. 11 is attached is referred to as a "diagnosis/treatment arm."

As shown in FIG. 10, in the present application example, a release operating element 501 is disposed at an appropriate place of the manipulation inputter 210 of the remote controller 20.

As shown in FIGS. 3, 4, 6, and 10, when the operator S manipulates the release operating element 501 of the manipulation inputter 210, the release operating element 501 outputs a release signal, and the release signal is input to the first controller 31 through the second controller 32. The first controller 31 controls the motor M to open the pair of claws (hereinafter referred to as a "holder") 150c of the holding instrument (auxiliary instrument)150 and controls the operation of the diagnosis/treatment arm 130A such that the holding instrument 150 moves away from the target person P as described below.

Figure 11:
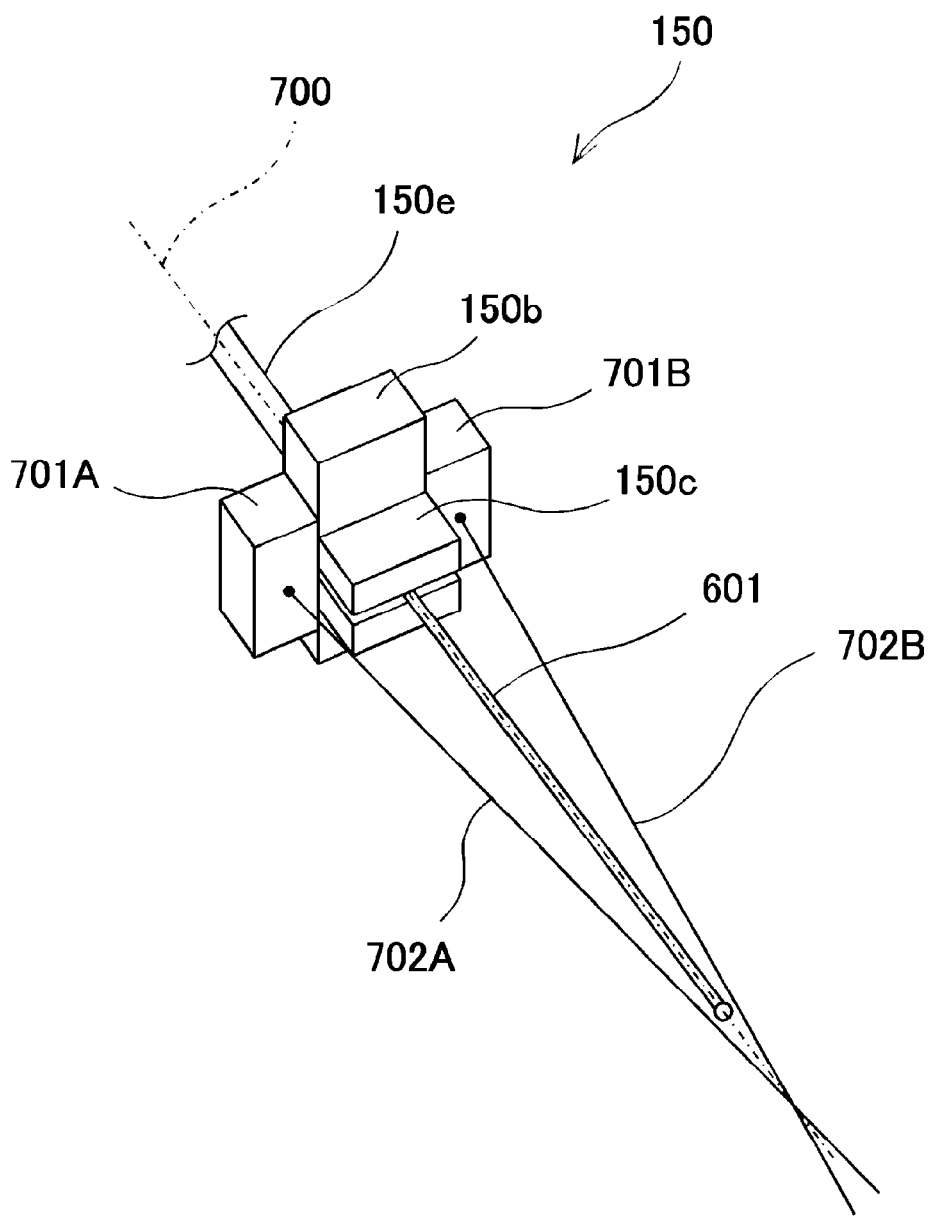
FIG. 11 is an external view showing one example of the configuration of a holding instrument (auxiliary instrument) of FIG. 9.

FIG. 11 is an external view showing one example of the configuration of the holding instrument 150 of FIG. 9. As shown in FIG. 11, in the holding instrument 150, a pair of laser beam indicators (laser pointers) 701A and 701B are disposed at the claw holding body 150b. The number of laser beam indicators may be three or more. The size of an irradiation spot of the laser beam is suitably selected. The pair of laser beam indicators 701A and 701B are located at both sides of the claw holding body 150b in a predetermined open-close direction of the pair of claws 150c of the claw holding body 150b. The pair of laser beam indicators 701A and 701B are arranged such that the laser beam emitted from the laser beam indicator 701A and the laser beam emitted from the laser beam indicator 701B intersect with each other and are located on the same plane as a central axis 700 of the holder (the pair of claws) 150c. The central axis 700 of the holder (the pair of claws) 150c is defined as, for example, a virtual axis which coincides with a central axis of the columnar coupler 150e and extends on a virtual plane with which the pair of claws 150c are closed to come into contact. Herein, a first end of a swab 601 is held by the holder 150c such that the swab 601 extends along the central axis 700. The swab 601 may extend in the vicinity of the central axis 700.

For example, the pair of laser beam indicators 701A and 701B are arranged such that a laser beam 702A emitted from the laser beam indicator 701A and a laser beam 702B emitted from the laser beam indicator 701B intersect with each other in a region beyond a tip (second end) of the swab 601 in a direction from the first end held by the holder 150c toward the second end of the swab 601. With this, a distance between an irradiation part of the target person P and the swab 601, i.e., a distance between a specimen collection part of the target person P and the swab 601 can be determined based on an interval between the irradiation spots (see FIG. 13; the irradiation spots are not shown) on the target person P by the pair of laser beams 702A and 702B.

As shown in FIG. 6, the pair of laser beam indicators 701A and 701B include, for example, power supplies (for example, batteries), and on and off of the power supplies are controlled through the second controller 32 and the first controller 31 by the operator S who manipulates a corresponding operating element (not shown) of the manipulation inputter 210.

Figure 12:
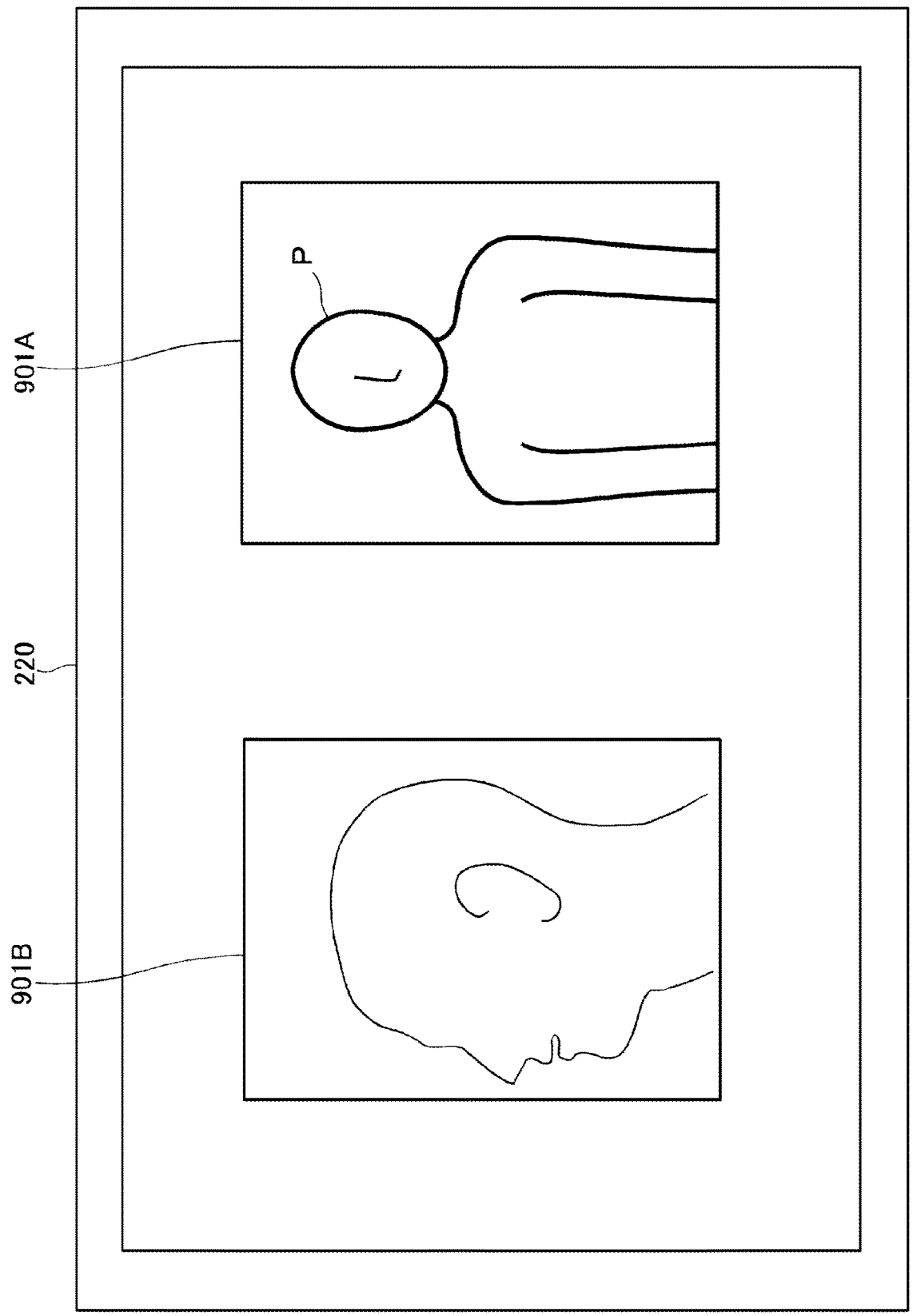
FIG. 12 is a schematic diagram showing an image taken by a first imager and an image taken by an auxiliary imager which are displayed on a display of the remote controller.

FIG. 12 is a schematic diagram showing an image 901A taken by the first imager 151A and an image 901B taken by the auxiliary imager 151B which are displayed on the display 220 of the remote controller 20.

As shown in FIGS. 6, 9, 10, and 12, as with the first imager 151A, the operation of the auxiliary imager 151B is controlled through the second controller 32 and the first controller 31 by the operator S who manipulates a corresponding operating element (not shown) of the manipulation inputter 210. As with the first imager 151A, the image 901B taken by the auxiliary imager 151B is transmitted to the second controller 32 through the first controller 31 and is displayed on the display 220 by the second controller 32.

The image taken by the auxiliary imager 151B is displayed alone or in combination with another image.

In the present application example, for example, the target person P sits on a chair, and a sterilized swab (hereinafter simply referred to as a "swab") is inserted into a nose or a mouth of the target person P. Thus, the specimen of the infectious disease is collected by the swab. When the swab is inserted into the nose, a nasopharynx swab fluid (mucus, nasal mucus, etc.) is collected. When the swab is inserted into the mouth, a throat swab fluid (mucus, phlegm, etc.) or saliva in the oral cavity is collected. At the time of the collection of the specimen, the image of the specimen collection part of the target person P is taken by the first imager 151A or the auxiliary imager 151B, and the taken image is displayed on the display 220. Herein, the image of the specimen collection part of the target person P is taken by the first imager 151A. When the swab is inserted into the nose, an imaging target may be the nasal cavity of the target person P. When the swab is inserted into the mouth, the imaging target may be the oral cavity of the target person P. For example, when a specimen (sputum, etc.) derived from the lower airway is collected by a suction catheter, the imaging target is the oral cavity of the target person P. In this case, for example, the suction catheter is held and handled by the auxiliary instrument 150 (holding instrument) of the second robotic arm 130B.

The following will describe one example of the PCR test using the diagnosis/treatment support robot system 1 when the swab is inserted into the nose.

First, the operator S performs manipulation so as to move the first imaging arm 130C to take an image of a front side of the face of the target person P by the first imager 151A and move the auxiliary imaging arm 130D to take an image of a lateral side of the face of the target person P by the auxiliary imager 151B. With this, as shown in FIG. 12, the image 901A taken by the first imager 151A and the image 902 taken by the auxiliary imager 151B are displayed on the display 220 of the remote controller 20.

On the other hand, the image of the face of the operator S is taken by the second imager 233, and the taken image is displayed on the display 173 of the surgical manipulator 6.

Next, for example, the operator S makes simple medical inquiries to the target person P while watching the display 220. For example, the operator S asks "How are you feeling?" Then, this inquiry is acquired by the second microphone 232, and the first speaker 171 outputs the sounds of this inquiry. The target person P answers "I have a slight fever" while watching the display 173. Then, this answer is acquired by the first microphone 172, and the second speaker 231 outputs the sounds of this answer. The operator S listens to this answer and says "I see. Let's have a medical examination," and the target person P says "Yes, please."

Next, the operator S starts the collection of the specimen.

Figure 13:
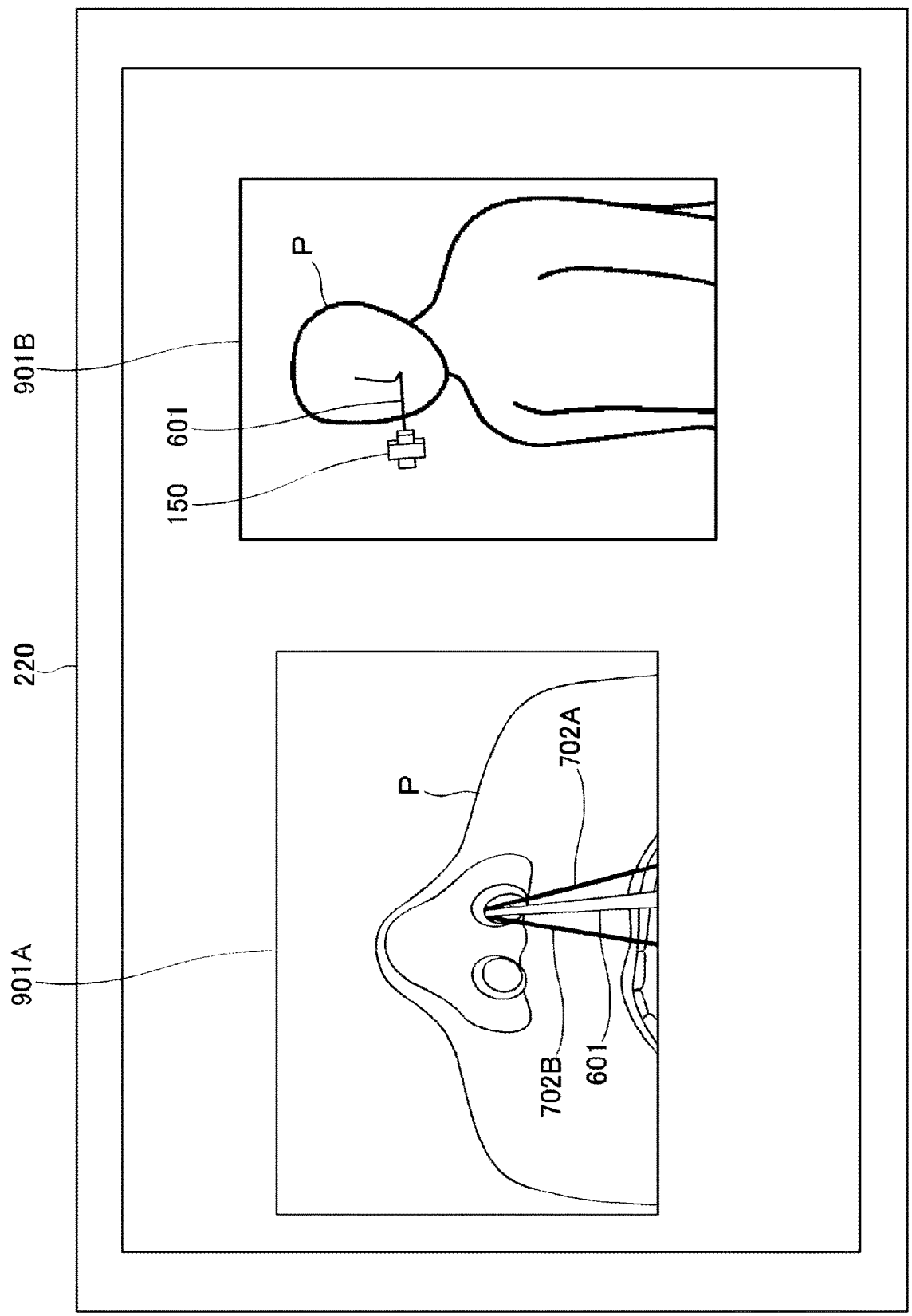
FIG. 13 is a schematic diagram showing an image taken by the first imager and an image taken by the auxiliary imager which are displayed on the display of the remote controller when collecting a specimen.

FIG. 13 is a schematic diagram showing the image 901A taken by the first imager 151A and the image 901B taken by the auxiliary imager 151B which are displayed on the display 220 of the remote controller 20 at the time of the collection of the specimen.

As shown in FIG. 13, at the time of the collection of the specimen, the operator S performs manipulation so as to move the first imaging arm 130C to take the zoom-up image 901A of the nose of the target person by the first imager 151A from the front side of the target person. Then, the operator S performs manipulation so as to move the auxiliary imaging arm 130D to take the image 901B of an oblique lateral side of the face of the target person P by the auxiliary imager 151B.

While confirming a distance between the swab 601 and the back of the nose as the specimen collection part on the zoom-up image 901A of the nose based on the irradiation spots (not shown) of the laser beams 702A and 702B of the pair of laser beam indicators 701A and 701B, the operator S manipulates the diagnosis/treatment arm 130A to insert the swab 601 into the back of the nose, wipe the back of the nose with the tip of the swab 601, and thus, collect the specimen. At this time, the operator S watches the reaction of the target person P regarding the collection of the specimen by the image 901B showing the oblique lateral side of the face (i.e., whether the target person P frowns, moves his/her face backward, or is calm).

Then, the operator S manipulates the diagnosis/treatment arm 130A to pull out the swab, which has collected the specimen, from the nose of the target person P and store the swab in a predetermined container.

When an emergency occurs in the process of collecting the specimen, the operator S manipulates the release operating element 501 of the manipulation inputter 210. With this, the holder 150c of the holding instrument 150 opens to release the swab 601, and the diagnosis/treatment arm 130A operates such that the holding instrument 150 moves away from the target person P.

In the present application example, the operator S can collect the specimen while confirming the distance between the swab 601 and the specimen collection part by the zoom-up image 901A of the nose and knowing the reaction of the target person regarding the collection of the specimen by the image 901B showing the oblique lateral side of the face. Therefore, the operator S can collect the specimen without hurting the target person. Moreover, the target person P can be protected from the emergency. When a doctor is the operator S or when a doctor is beside the operator S, the doctor can perform communication (make medical inquiries) regarding the diagnosis by the sounds.

Modified Example 1

Figure 14:
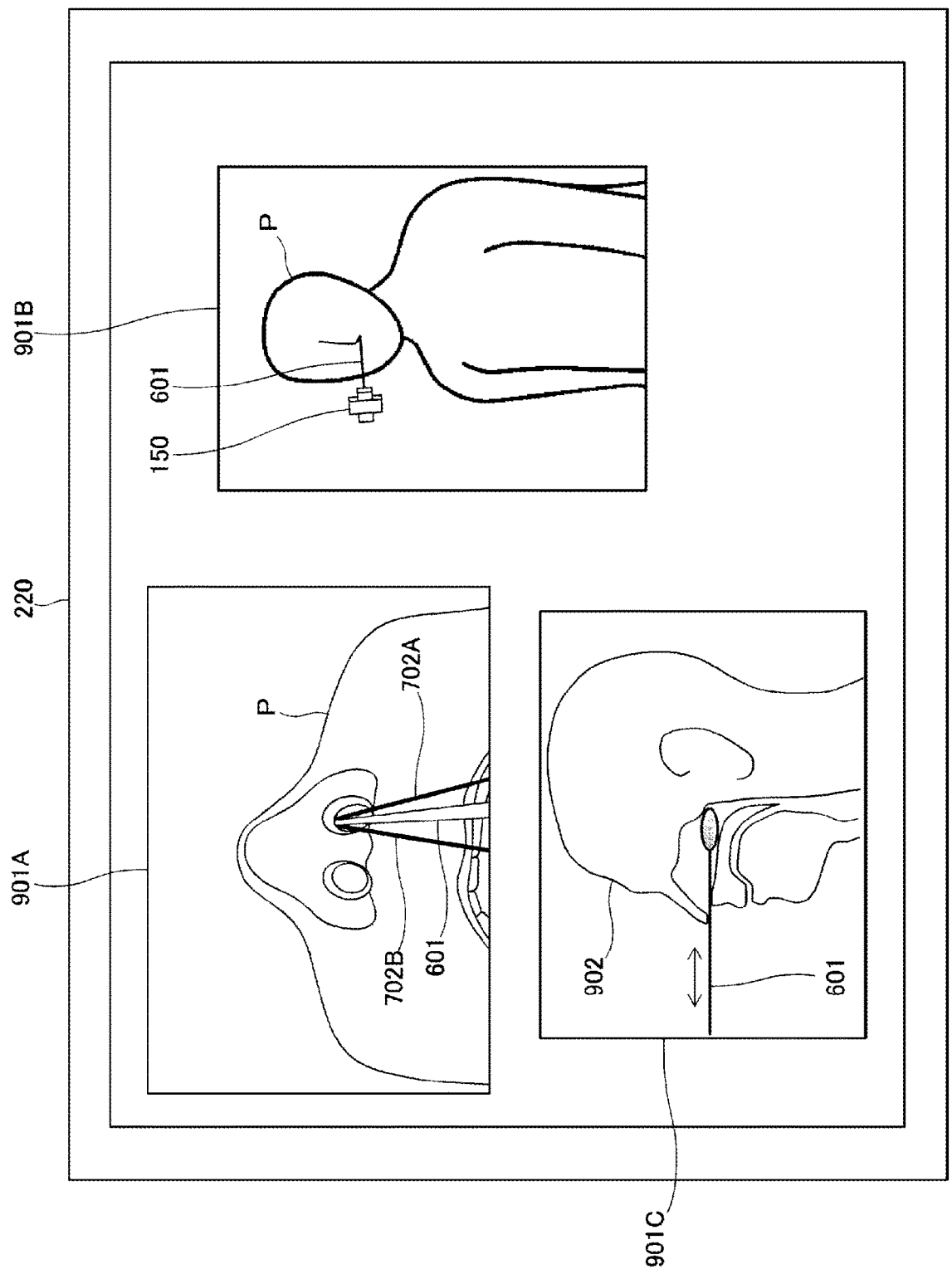
FIG. 14 is a schematic diagram showing an image taken by the first imager, an image taken by the auxiliary imager, and a first swab insertion degree model which are displayed on the display of the remote controller.

FIG. 14 is a schematic diagram showing the image 901A taken by the first imager 151A, the image 901B taken by the auxiliary imager 151B, and a first swab insertion degree model 901C, which are displayed on the display 220 of the remote controller 20.

As shown in FIG. 14, in Modified Example 1, together with the image 901A taken by the first imager 151A and the image 901B taken by the auxiliary imager 151B, the display 220 displays a swab insertion degree model that shows the degree of insertion of the swab 601 into the body of the target person P. Herein, the first swab insertion degree model 901C is displayed as the swab insertion degree model.

In the first swab insertion degree model 901C, the swab 601 is shown in the nasal cavity of a face lateral side model 902 that imitates the lateral side of the face of the target person P. Then, the position of the swab 601 is changed in accordance with the degree of actual insertion of the swab 601 into the nose by the holding instrument 150.

In this case, the second controller 32 determines the position of the swab 601 in the first swab insertion degree model 901C, based on the position of the swab 601 and an assumed position of the face of the target person P in a coordinate system of the diagnosis/treatment support robot 10. The position of the swab 601 and the assumed position of the face of the target person P may be input from the first controller 31. For example, a position sensor may be mounted on the holding instrument 150, and the position of the swab 601 in the first swab insertion degree model 901C may be determined based on the output of the position sensor. In Modified Example 1, it is preferable to prepare a chair which is adjustable such that the face of the target person P is located at the above assumed position. One example of such chair is a chair which can automatically adjust the height of a seat thereof and can fix the head of the target person P. The image 901A or the image 901B may be omitted.

According to Modified Example 1, the operator S can smoothly insert the swab 601 into the specimen collection part of the nose of the target person P while watching the first swab insertion degree model 901C. Therefore, the specimen can be quickly and accurately collected.

Modified Example 2

Figure 15:
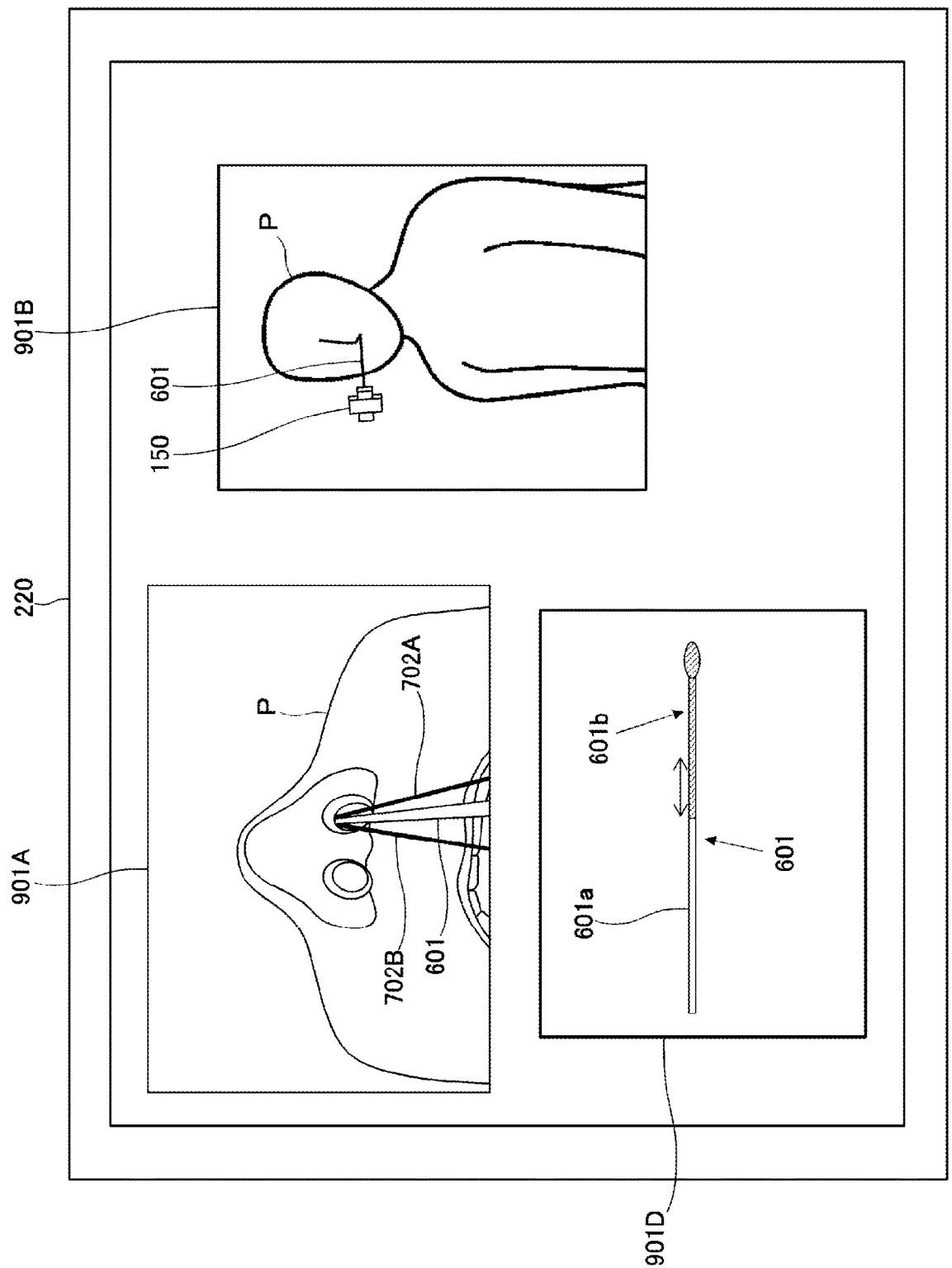
FIG. 15 is a schematic diagram showing an image taken by the first imager, an image taken by the auxiliary imager, and a second swab insertion degree model which are displayed on the display of the remote controller.

FIG. 15 is a schematic diagram showing the image 901A taken by the first imager 151A, the image 901B taken by the auxiliary imager 151B, and a second swab insertion degree model 901D, which are displayed on the display 220 of the remote controller 20.

As shown in FIG. 15, in Modified Example 2, the second swab insertion degree model 901D is displayed as the swab insertion degree model.

In the second swab insertion degree model 901D, a portion 601a that is not in the nose and a portion 601b that is in the nose are shown on the model of the swab 601. Then, a boundary between these portions is changed in accordance with the degree of actual insertion of the swab 601 into the nose by the holding instrument 150. In this case, for example, the portion 601b in the nose may be displayed in color.

The position of the boundary between these portions is determined in the same manner as Modified Example 1. The image 901A or the image 901B may be omitted.

According to Modified Example 2, the operator S can smoothly insert the swab 601 into the specimen collection part of the nose of the target person P while watching the second swab insertion degree model 901D. Therefore, the specimen can be quickly and accurately collected.

Other Modified Example

As with Modified Examples 1 and 2 in which the swab is inserted into the nose, when the swab is inserted into the mouth, a swab insertion degree model that shows the degree of insertion of the swab 601 into the oral cavity of the target person P may be displayed on the display 220.

Other Embodiments

Each of the diagnosis/treatment support robot system 1 according to the above embodiment and the diagnosis/treatment support robot system 1 according to the application example to the PCR test may be located in a medical movable body (for example, a hospital ship or a railcar).

The second controller 32 may have a learning function. Specifically, the second controller 32 may include a manipulation storage that stores all manipulation inputs to the manipulation inputter 210 by the operator S or a manipulation learning unit that uses machine learning to learn the manipulation inputs to the manipulation inputter 210 by the operator S.

When the second controller 32 includes the manipulation storage, the stored manipulation inputs that are output from the manipulation storage are used for the operation control of the diagnosis/treatment support robot 10 instead of the manipulation inputs from the manipulation inputter 210.

When the second controller 32 includes the manipulation learning unit, at the time of the learning, the manipulation inputs from the manipulation inputter 210 and suitable operation data, such as the display image of the display 220, are input as learning data to the manipulation learning unit. After the leaning is completed, the learned manipulation inputs that are output from the manipulation learning unit are used for the operation control of the diagnosis/treatment support robot 10 instead of the manipulation inputs from the manipulation inputter 210.

With this, the diagnosis/treatment support robot 10 can autonomously perform the auxiliary practice of the diagnosis or the auxiliary practice of the treatment.

From the foregoing explanation, many modifications and other embodiments of the present disclosure are obvious to one skilled in the art. Therefore, the foregoing explanation should be interpreted only as an example.

Other Operational Advantages of Embodiment

As described above, according to the embodiment of the present disclosure, the surgical manipulator 6 may include a plurality of the robotic arms 130.

According to this configuration, the operator S can move at least two robotic arms 130 as with human arms. Therefore, even when the auxiliary practice of the diagnosis or the auxiliary practice of the treatment is complex, the operator S can appropriately perform the auxiliary practice of the diagnosis or the auxiliary practice of the treatment.

The auxiliary instrument 150 may have four or more degrees of freedom of movement of the auxiliary instrument 150, and the instrument mount 137 may allow the auxiliary instrument 150 to operate in four or more degrees of freedom of movement thereof.

According to this configuration, the auxiliary practice of the diagnosis or the auxiliary practice of the treatment which is complex can be appropriately performed by operating the auxiliary instrument 150 having four or more degrees of freedom of movement thereof.

The surgical manipulator 6 may be at the cart 70 that can autonomously travel.

According to this configuration, the diagnosis/treatment support robot 10 (surgical manipulator 6) can move between the normal area and the isolation area.

The isolation area that isolates an infected person or a suspected infected person may include an area where at least either one of the auxiliary practice of the diagnosis of the infectious disease or the auxiliary practice of the treatment of the infectious disease is performed for the target person P. The surgical manipulator 6 and the cart 70 may move to the isolation area from the normal area that is not the isolation area. The surgical manipulator 6 and the cart 70 may be disinfected before entering into the isolation area from the normal area or after getting out from the isolation area toward the normal area.

According to this configuration, the surgical manipulator 6 and the cart 70 can enter into the isolation area after the disinfection, or the surgical manipulator 6 and the cart 70 which have gotten out from the isolation area can move to the normal area after the disinfection. Therefore, the infection of a person due to the surgical manipulator 6 and the cart 70 can be prevented.

The auxiliary instrument 150 may be a holding instrument that holds the diagnosis/treatment tool.

According to this configuration, in the auxiliary practice of the diagnosis or the auxiliary practice of the treatment, the medical worker holds the diagnosis/treatment tool with his/her hands in many cases. Therefore, the holding instrument can hold the diagnosis/treatment tool so as to widely perform the auxiliary practice of the diagnosis or the auxiliary practice of the treatment in place of the medical worker. Regarding industrial robots, there are various types of hands (end effectors) that can appropriately hold various types of members. Therefore, various types of holding instruments can be obtained by suitably modifying various types of hands.

The diagnosis/treatment tool may be a tool that collects a specimen regarding an infectious disease of the target person P; a drip infusion tool; a blood collecting tool; or a cannula of an artificial heart and lung apparatus.

According to this configuration, practices especially necessary in the diagnosis of the infectious disease and the treatment of the infectious disease can be performed by using the surgical manipulator.

The robotic arm 30 may be manipulated by the operator S in a master-slave mode.

According to this configuration, the robotic arm 130 can be suitably manipulated.

The hold facilitating jig 81, 82 by which the holding instrument easily holds the diagnosis/treatment tool may be attached to the diagnosis/treatment tool.

Some of the diagnosis/treatment tools are difficult for the holding instrument to directly hold. Examples of such tools include: fragile tools (syringes, containers, and the like made of glass); too thin or too small tools (thin tubes and the like); and tools that are difficult to be held since the shapes thereof are complex. In this case, a jig that is easy for the holding instrument to hold may be attached to such diagnosis/treatment tool in advance. With this, the holding instrument holds the jig, and as a result, the holding instrument can easily hold the diagnosis/treatment tool.

The diagnosis/treatment support robot system 1 may further include the hold facilitating jigs 81 and 82.

According to this configuration, the diagnosis/treatment tool that is difficult to directly be held can be easily held by the auxiliary instrument 150.

The diagnosis/treatment support robot 10 may include: the first speaker 171 that transmits to the target person P, the voice of the operator S which is acquired by the second microphone 232; and the first microphone 172 that acquires the voice of the target person P. The remote controller 20 may include: the second speaker 31 that transmits to the operator S, the voice of the target person P which is acquired by the first microphone 172; and the second microphone 232 that acquires the voice of the operator S.

According to this configuration, the operator S can appropriately perform the auxiliary practice of the diagnosis or the auxiliary practice of the treatment while communicating with the target person P through dialogue.

The diagnosis/treatment support robot 10 may be in the isolation area that isolates an infected person or a suspected infected person, and the remote controller 20 may be in the normal area that is not the isolation area.

According to this configuration, the surgical manipulator 6 of the diagnosis/treatment support robot 10 located in the isolation area can be manipulated by the remote controller 20 located in the normal area. Therefore, the operator S can be prevented from being infected with the infectious disease.

The holding instrument 150 may include the laser beam indicators 701A and 701B, and the laser beam indicators 701A and 701B may be located such that the laser beam 702A emitted from the laser beam indicator 701A and the laser beam 702B emitted from the laser beam indicator 701B intersect with each other.

According to this configuration, in the case where the auxiliary practice of the diagnosis or the auxiliary practice of the treatment is performed for the target person P by using the diagnosis/treatment tool held by the holding instrument 150, when the target person P is irradiated with the laser beams 702A and 702B, the distance between the irradiation part of the target person P and the diagnosis/treatment tool, i.e., the distance between the target part for the auxiliary practice and the diagnosis/treatment tool can be determined based on the interval between the irradiation spots on the target person P by the laser beams 702A and 702B. With this, the auxiliary practice of the diagnosis or the auxiliary practice of the treatment can be appropriately performed.

The diagnosis/treatment tool having a rod shape may be the swab 601 that collects the specimen of the infectious disease from the target person P. The holding instrument 150 may include the holder 150c that can hold the first end of the swab 601. The holder 150c and the laser beam indicators 701A and 701B may be located such that a region where the laser beams 702A and 702B emitted from the laser beam indicators 701A and 701B intersect with each other is located closer to the second end of the swab 601 than to the holder 150c in a direction from the first end held by the holder 150c toward the second end of the swab 601.

According to this configuration, the distance between the irradiation part of the target person P and the swab 601, i.e., the distance between the specimen collection part and the swab 601 can be suitably obtained based on the interval between the irradiation spots on the target person P by the laser beams 702A and 702B.

The diagnosis/treatment support robot system 1 may include the auxiliary imager 151B that takes the image of the lateral side of the face of the target person P. The first imager 151A may take the image of the front side of the face of the target person P. The second display 220 may display the image taken by the first imager 151A and/or the image taken by the auxiliary imager 151B. Herein, the auxiliary imager 151B may be attached to the robotic arm 130, another robot, a wall of the isolation area, or the like.

According to this configuration, when collecting the specimen of the infectious disease from the nose or the throat of the target person P by using the swab 601, the first imager 151A exclusively takes the zoom-up image of the nose or the mouth of the target person P from the front side. Therefore, the operator S cannot know the reaction of the target person P regarding the collection of the specimen (whether the target person P frowns, moves his/her face backward. or is calm). However, according to this configuration, since the auxiliary imager 151B takes the image of the lateral side of the face of the target person P, the operator can know the reaction of the target person P regarding the collection of the specimen based on the lateral side of the face in the taken image. Therefore, the operator S can collect the specimen without hurting the target person P.

The robotic arms 130 may further include the auxiliary imaging arm 130D including the instrument mount 137 to which the auxiliary imager 151B is attached.

According to this configuration, when the operator S manipulates the auxiliary imaging arm 130D, the image of the lateral side of the face of the target person P can be appropriately taken from a desired angle and a desired distance.

The second display 220 may display the swab insertion degree model 901C, 901D at least together with the image taken by the first imager 151A or the image taken by the auxiliary imager 151B, and the swab insertion degree model 901C, 901D may indicate the degree of insertion of the swab 601 into the body of the target person P. Herein, for example, the degree of insertion of the swab may be determined based on the position of the swab 601 and the assumed position of the face of the target person P in the robot coordinate system.

According to this configuration, the operator S can smoothly insert the swab 601 into the specimen collection part in the body of the target person P while watching the swab insertion degree model 901C, 901D. As a result, the specimen can be quickly and accurately collected.

The remote controller 20 may include the release operating element 501. When the release operating element 501 is manipulated, the surgical manipulator 6 may release the swab 601 held by the holding instrument attached to the instrument mount 137 of the diagnosis/treatment arm.

According to this configuration, when the operator S manipulates the release operating element 501 in emergency (for example, in a case where the surgical manipulator abnormally operates), the swab 601 held by the holding instrument is released. Therefore, the target person P can be protected from the emergency.

When the release operating element 501 is manipulated, the surgical manipulator 6 may operate the diagnosis/treatment arm to move the holding instrument away from the target person P.

According to this configuration, when the operator S manipulates the release operating element 501 in emergency, the swab 601 held by the holding instrument is released, and the holding instrument moves away from the target person P. Therefore, the target person P can be more suitably protected from the emergency.

INDUSTRIAL APPLICABILITY

The diagnosis/treatment support robot, the diagnosis/treatment support robot system, and the diagnosis/treatment support method according to the present disclosure are useful as a diagnosis/treatment support robot, a diagnosis/treatment support robot system, and a diagnosis/treatment support method, each of which performs at least either one of a diagnosis or a treatment in place of a medical worker and therefore can prevent the medical worker from being infected with an infectious disease.

The invention claimed is:
1. A diagnosis/treatment support robot comprising a surgical manipulator that is capable of being remotely manipulated, wherein:
the surgical manipulator includes a robotic arm;
the robotic arm includes an instrument mount at a tip thereof;
a surgical instrument for surgery of a patient is attached to the instrument mount;
an auxiliary instrument is attachable to the instrument mount;

the auxiliary instrument is an instrument other than the surgical instrument;

the auxiliary instrument is an instrument for at least either one of an auxiliary practice of a diagnosis of an infectious disease for a target person or an auxiliary practice of a treatment of the infectious disease for the target person;

the surgical manipulator is configured to be manipulated to hold a swab by a tip of the auxiliary instrument; and a specimen of the infectious disease from the target person is collected by the swab held by the tip of the auxiliary instrument or in a process of collecting the specimen of the infectious disease from the target person, the surgical manipulator is configured to manipulate the surgical manipulator to release the swab from the auxiliary instrument and move the auxiliary instrument away from the target person.

2. The diagnosis/treatment support robot according to claim 1, wherein:

the surgical manipulator includes a plurality of the robotic arms;

the auxiliary instrument has four or more degrees of freedom of movement of the auxiliary instrument; and the instrument mount allows the auxiliary instrument to operate in four or more degrees of freedom of movement thereof.

3. The diagnosis/treatment support robot according to claim 1, wherein:

an isolation area that isolates an infected person or a suspected infected person includes an area where at least either one of the auxiliary practice of the diagnosis of the infectious disease or the auxiliary practice of the treatment of the infectious disease is performed for the target person;

the surgical manipulator is at a cart that autonomously travels;

the surgical manipulator and the cart move to the isolation area from a normal area that is not the isolation area; and the surgical manipulator and the cart are disinfected before entering into the isolation area or after getting out from the isolation area.

4. The diagnosis/treatment support robot according to claim 1, wherein:

the robotic arm is manipulated by the operator in a master-slave mode;

the auxiliary instrument is a holding instrument that holds a diagnosis/treatment tool;

the diagnosis/treatment tool is a tool that collects a specimen regarding the infectious disease of the target person, a drip infusion tool, a blood collecting tool, or a cannula of an artificial heart and lung apparatus; and a hold facilitating jig by which the holding instrument easily holds the diagnosis/treatment tool is attached to the diagnosis/treatment too.

5. A diagnosis/treatment support robot system comprising:

a diagnosis/treatment support robot comprising a surgical manipulator that is remotely manipulated by an operator, wherein the surgical manipulator includes a robotic arm, the robotic arm includes an instrument mount at a tip thereof, a surgical instrument for surgery of a patient is attached to the instrument mount, an auxiliary instrument is attachable to the instrument mount, the auxiliary instrument is an instrument other than the surgical instrument, and the auxiliary instrument is an instrument for at least either one of an auxiliary practice of a diagnosis of an infectious disease for a target person or an auxiliary practice of a treatment of the infectious disease for the target person;

a remote controller by which the operator remotely manipulates the surgical manipulator of the diagnosis/treatment support robot; and a first imager that is attached to the instrument mount of the robotic arm of the surgical manipulator and takes an image of a state of a diagnosis/treatment area where the diagnosis/treatment for the target person is performed, wherein:

the surgical manipulator includes a plurality of the robotic arms;

the robotic arms includes a diagnosis/treatment arm including the instrument mount to which the auxiliary instrument is attached and an imaging arm including the instrument mount to which the first imager is attached;

the remote controller includes a second display that displays the image of the state of the diagnosis/treatment area which is taken by the first imager and a second imager that takes an image of the operator; and the surgical manipulator further includes a first display that displays the image of the operator which is taken by the second imager;

the holding instrument includes laser beam indicators;

the laser beam indicators are located such that laser beams emitted from the laser beam indicators intersect with each other;

the diagnosis/treatment tool is a swab that collects a specimen of the infectious disease from the target person;

the holding instrument includes a holder that holds a first end of the swab; and the holder and the laser beam indicators are located such that a region where the laser beams emitted from the laser beam indicators intersect with each other is located closer to a second end of the swab than the holder in a direction from the first end held by the holder toward the second end of the swab.

6. The diagnosis/treatment support robot system according to claim 5, wherein:

the diagnosis/treatment support robot includes a first speaker that transmits to the target person, voice of the operator which is acquired by a second microphone and a first microphone that acquires voice of the target person; and the remote controller includes a second speaker that transmits to the operator, the voice of the target person which is acquired by the first microphone and the second microphone that acquires the voice of the operator.

7. The diagnosis/treatment support robot system according to claim 5, wherein:

the diagnosis/treatment support robot is in an isolation area that isolates an infected person or a suspected infected person; and the remote controller is in a normal area that is not the isolation area.

8. The diagnosis/treatment support robot system according to claim 5, further comprising an auxiliary imager that takes an image of a lateral side of a face of the target person, wherein:
the first imager takes an image of a front side of the face of the target person; and
the second display displays the image taken by the first imager and/or the image taken by the auxiliary imager.

9. The diagnosis/treatment support robot system according to claim 8, wherein the robotic arms further include an auxiliary imaging arm including the instrument mount to which the auxiliary imager is attached.

10. The diagnosis/treatment support robot system according to claim 8, wherein the second display displays a swab insertion degree model at least together with the image taken by the first imager or the image taken by the auxiliary imager, the swab insertion degree model indicating the degree of insertion of the swab into a body of the target person.

11. The diagnosis/treatment support robot system according to claim 5, wherein:
the remote controller includes a release operating element; and
when the release operating element is manipulated, the surgical manipulator releases the swab held by the holding instrument attached to the instrument mount of the diagnosis/treatment arm.

12. The diagnosis/treatment support robot system according to claim 11, wherein when the release operating element is manipulated, the surgical manipulator operates the diagnosis/treatment arm to move the holding instrument away from the target person.

13. A diagnosis/treatment support method executed by circuitry of a diagnosis/treatment support robot, wherein:
the diagnosis/treatment support robot includes a surgical manipulator that is remotely manipulated by an operator;
the surgical manipulator includes a robotic arm;
the robotic arm includes an instrument mount at a tip thereof;
a surgical instrument for surgery of a patient is attached to the instrument mount;
an auxiliary instrument is attachable to the instrument mount;
the auxiliary instrument is an instrument other than the surgical instrument; and
the auxiliary instrument is an instrument for at least either one of an auxiliary practice of a diagnosis of an infectious disease for a target person or an auxiliary practice of a treatment of the infectious disease for the target person, and wherein
the diagnosis/treatment support method comprises:
attaching the auxiliary instrument instead of the surgical instrument to the instrument mount;
manipulating the surgical manipulator to hold a swab by a tip of the auxiliary instrument; and
collecting a specimen of the infectious disease from the target person by the swab held by the tip of the auxiliary instrument or in a process of collecting the specimen of the infectious disease from the target person, manipulating the surgical manipulator to release the swab from the auxiliary instrument and move the auxiliary instrument away from the target person.

14. The diagnosis/treatment support method according to claim 13, wherein an isolation area that isolates an infected person or a suspected infected person includes an area where at least either one of the auxiliary practice of the diagnosis of the infectious disease or the auxiliary practice of the treatment of the infectious disease is performed for the target person, and wherein
the diagnosis/treatment support method further comprises:
moving the surgical manipulator and the cart to the isolation area from a normal area that is not the isolation area; and
disinfecting the surgical manipulator and the cart before the surgical manipulator and the cart enter into the isolation area or after the surgical manipulator and the cart get out from the isolation area.

* * * * *